United States Patent
Laforest et al.

(10) Patent No.: US 11,179,033 B2
(45) Date of Patent: Nov. 23, 2021

(54) SYSTEM, METHOD AND APPARATUS FOR RETINAL ABSORPTION PHASE AND DARK FIELD IMAGING WITH OBLIQUE ILLUMINATION

(71) Applicant: ECOLE POLYTECHNIQUE FEDERALE DE LAUSANNE (EPFL), Lausanne (CH)

(72) Inventors: Timothé Laforest, Sivignon (FR); Dino Carpentras, Ecublens (CH); Christophe Moser, Lausanne (CH); Mathieu Künzi, Chêne-Bourg (CH); Francine Behar-Cohen, Paris (FR)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 167 days.

(21) Appl. No.: 16/300,937

(22) PCT Filed: May 12, 2017

(86) PCT No.: PCT/IB2017/052803
§ 371 (c)(1),
(2) Date: Nov. 12, 2018

(87) PCT Pub. No.: WO2017/195163
PCT Pub. Date: Nov. 16, 2017

(65) Prior Publication Data
US 2019/0290124 A1 Sep. 26, 2019

(30) Foreign Application Priority Data

May 13, 2016 (WO) .................. PCT/IB2016/052787
Nov. 11, 2016 (WO) .................. PCT/IB2016/056806

(51) Int. Cl.
*A61B 3/12* (2006.01)
*A61B 3/00* (2006.01)
*A61B 3/14* (2006.01)

(52) U.S. Cl.
CPC .............. *A61B 3/12* (2013.01); *A61B 3/0008* (2013.01); *A61B 3/14* (2013.01)

(58) Field of Classification Search
CPC ............ A61B 3/12; A61B 3/0008; A61B 3/14
(Continued)

(56) References Cited

U.S. PATENT DOCUMENTS

| | | | | |
|---|---|---|---|---|
| 5,099,354 A | * | 3/1992 | Lichtman | G02B 21/0028 359/227 |
| 8,237,835 B1 | * | 8/2012 | Muller | G02B 21/008 348/296 |
| 2009/0153798 A1 | * | 6/2009 | Dick | A61B 5/0261 351/206 |

FOREIGN PATENT DOCUMENTS

EP         1 964 510         9/2008

OTHER PUBLICATIONS

Tian et al., "Quantitative differential phase contrast imaging in an LED array microscope", Optics Express vol. 23, Issue 9, p. 11394-11403 (2015) (Year: 2015).*
Schmitt, et al., "Differential absorption imaging with optical coherence tomography", J. Opt. Soc. Am. A, Sep. 1998, vol. 15, No. 9, pp. 2288-2296. (9 pages) (Year: 1998).*
Tian Lei, et al., "Quantitative differential phase contrast imaging in an LED array microscope", Database Medline, US National Library of Medicine (NLM), May 4, 2015, vol. 23, XP-002774005. (1 page).

(Continued)

*Primary Examiner* — Marin Pichler
*Assistant Examiner* — Mitchell T Oestreich
(74) *Attorney, Agent, or Firm* — Nixon & Vanderhye P.C.

(57) ABSTRACT

A method for imaging a tissue of an eye, the method including the steps of providing oblique illumination to the eye by a plurality of light emitting areas of a light delivery device, the plurality of light emitting areas being independently controllable and arranged to direct light towards at least one of a retina and an iris of the eye, causing an output beam from light backscattered from the at least one of the retina and the iris by the oblique illumination, capturing the
(Continued)

output beam with an imaging system to provide a sequence of images of a fundus of the eye, and retrieving a phase and absorption contrast image from the sequence of images of the fundus, wherein the sequence of images of the fundus of the step of capturing is obtained by sequentially turning on one or more of the plurality of light emitting areas at a time in the step of providing the oblique illumination.

18 Claims, 43 Drawing Sheets

(58) Field of Classification Search
USPC .......................................................... 351/206
See application file for complete search history.

(56) References Cited

OTHER PUBLICATIONS

J.M. Schmitt, et al., "Differential absorption imaging with optical coherence tomography", J. Opt. Soc. Am. A, Sep. 1998, vol. 15, No. 9, pp. 2288-2296. (9 pages).
International Search Report for PCT/IB2017/052803 dated Oct. 10, 2017. (5 pages).
Written Opinion of the ISA for PCT/IB2017/052803 dated Oct. 10, 2017. (6 pages).

* cited by examiner

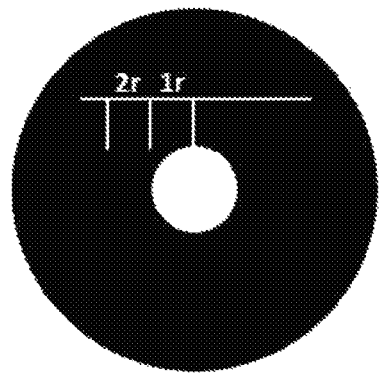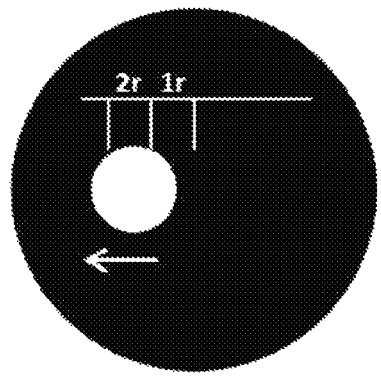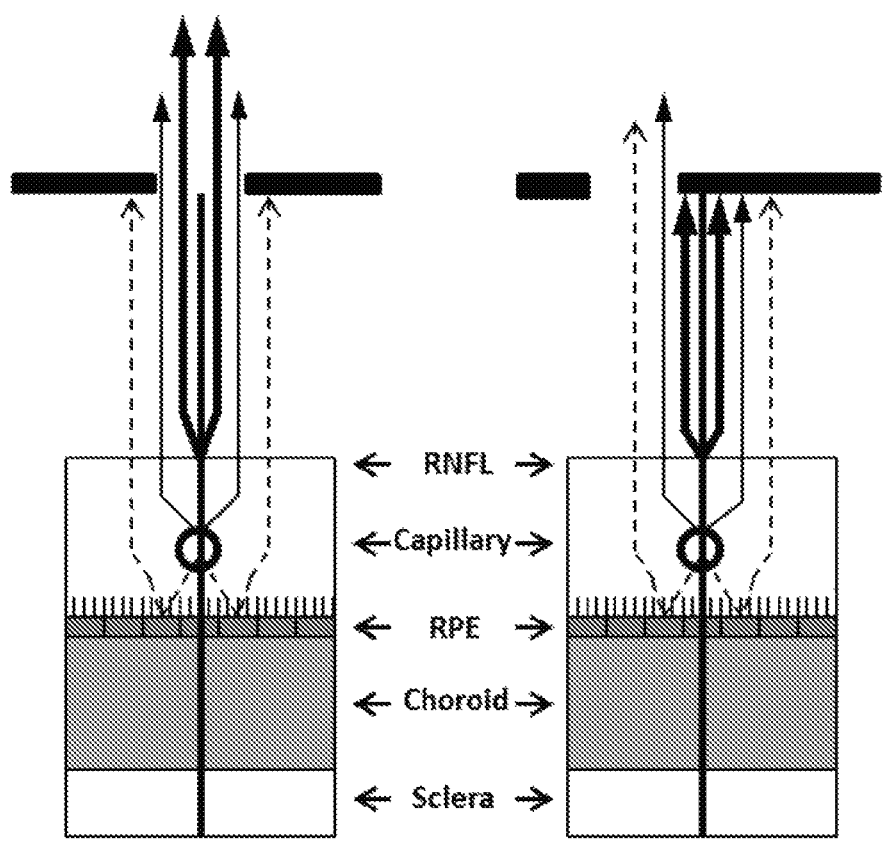
FIGs. 5A and 5B
BACKGROUND ART example of in vivo human eye fundus image with transcleral illumination intensity, 1 LED illumination,
NA=0.25 phase, DHM, NA=0.4    phase,
NA=0.25 (0.5 effective)

SYSTEM, METHOD AND APPARATUS FOR RETINAL ABSORPTION PHASE AND DARK FIELD IMAGING WITH OBLIQUE ILLUMINATION

CROSS-REFERENCE TO RELATED APPLICATIONS

This application is the U.S. national phase of International Application No. PCT/IB2017/052803, filed May 12, 2017, which designated the U.S. and claims priorities to PCT/IB2016/052787, filed May 13, 2016, and PCT/IB2016/056806, filed Nov. 11, 2016, the entire contents of each of which are hereby incorporated by reference.

FIELD OF THE INVENTION

The present invention relates to high resolution quantitative and qualitative absorption, phase and dark field imaging of the retina by the use of oblique illumination.

BACKGROUND

Standard photography relies on the difference in absorption of different features for providing contrast. This is also the case in conventional funduscopy where blood vessels, photoreceptors and other retinal structures are observed thanks to their different reflectivity values that provide intensity modulation at the sensor plane. This is not the case for most of the cells lying in the inner retina (ganglions, nuclear and plexiform layers), whose absorption and scattering values are so low to show almost no contrast even at high resolution. Furthermore, the intensity modulation of these features is negligible with respect to the background modulation signal (due to underlying features) in combination with noise. Even with optical coherence tomography (OCT), the weak contrast of these cells make the retina appear as a smooth layer, almost free of features.

Tian et al. showed that images of a phase sample (sample with weakly absorptive features) acquired with different angles of illumination can be used to obtain a single phase image of the sample (L. Tian and L. Waller, "Quantitative differential phase contrast imaging in an LED array microscope," Opt. Exp. 23, 9, pp. 11394-11403 (2015)). In their method, where illumination is provided in transmission, they used a Wemier filter based algorithm to reconstruct the phase image. Such a method is not directly applicable to living biological media, since transmission illumination is, in general, not possible. A solution of this problem has been proposed by Ford et al. (T. N Ford, K. K Chu and J. Mertz, "Phase-gradient microscopy in thick tissue with oblique back-illumination," Nat. methods, 9, 12 (2012)), where the light from the deep layer of the sample, is used as a secondary source illuminating the top layers in a transmission fashion. For providing oblique illumination, Ford et al. shined light in the sample at a point pi, showing that the area at a certain distance d was back illuminated in an oblique fashion. By subtracting the pictures obtained with 2 opposite illumination points it was possible to reconstruct a phase contrast image of the sample.

Dark field images of the retina have been studied for the case of illumination through the pupil. In these studies, an enhanced contrast of the vasculature has been shown (D. Scoles, Y. N. Sulai and A. Dubra "In vivo dark-field imaging of the retinal pigment epithelium cell mosaic," Biomed. Opt. Exp. 4, 9, pp. 1710-1723 (2013), T. Y. P. Chui, D. A. VanNasdale, and S. A. Burns, "The use of forward scatter to improve retinal vascular imaging with an adaptive optics scanning laser ophthalmoscope," Biomed. Opt. Exp. 3, 10, pp. 2537-2549 (2012)).

By combining several dark field images of a sample can lead to an image containing the partial derivative of the phase information by subtracting two images taken from asymmetric illumination. This has been shown either in transmission for a microscope (Z. Liu, S. Liu and L. Waller "Real-time brightfield, darkfield, and phase contrast imaging in a light emitting diode array microscope," J. of Biomed. Opt. 19, 10, 106002 (2014)) or in reflection using oblique back-illumination in an endoscope (Int. Pat. Pub. No. WO 2013/148360, T. N Ford, K. K Chu and J. Mertz, "Phase-gradient microscopy in thick tissue with oblique back-illumination," Nat. Methods, 9, 12 (2012)). Moreover, knowing the angle of illumination of the sample i.e. its spectrum, a quantitative phase information can be recovered using a weak object transfer function model (S. B. Mehta and C. J. R. Sheppard, "Quantitative phase-gradient imaging at high resolution with asymmetric illumination-based differential phase contrast," Opt. Lett. 34, 13, pp. 1924-1926 (2009), L. Tian and L. Waller, "Quantitative differential phase contrast imaging in an LED array microscope," Opt. Exp. 23, 9, pp. 11394-11403 (2015)) or a Fourier ptychography algorithm (Int. Pat. Pub. No. WO 2015/179452, G. Zheng, R. Horstmeyer, and C. Yang, "Wide-field, high-resolution Fourier ptychographic microscopy"). A similar approach can be used also for reconstructing a 3D picture of the sample ("Microscopy refocusing and dark-field imaging by using a simple LED array" G. Zheng, C. Kolner, and C. Yang, Optics Letters, pp. 3987-3989 (2011)).

Finally, processing the images also allows correcting the eye's aberrations optimizing Fourier properties of the images (U.S. Pat. No. 8,731,272, Z. Phillips, M. Chen, L. Waller, "Quantitative Phase Microscopy with Simultaneous Aberration Correction," Optics in the Life Sciences Congress, OSA Technical Digest (online), Optical Society of America, 2017), paper JTu5A.2.

Few attempts have been reported to obtain dark field images with higher contrast that obtained via the trans-pupil illumination described above.

One study is using transscleral illumination, i.e. light is provided to the fundus via illumination through the sclera, to obtain higher contrast dark field images of the retina (A. Schalenbourg, L. Zografos "Pitfalls in colour photography of choroidal tumours." Eye. 2013, Vol. 27(2), pp. 224-229). In U.S. Pat. No. 7,387,385 in FIG. 21, U.S. Pat. Pub. No. 2007/0159600, and U.S. Pat. Pub. No. 2007/0030448 in FIG. 22, a transscleral illumination with several differing wavelength (red, green, blue) is used to make one image with several wavelength simultaneously. This resulting image is used to diagnose choroidal tumors. Contrary to full field illumination through the eye lens (called transpupilary illumination), transscleral illumination allows to collect light only coming from underneath the ~100 um thick first layer of the retina. This is because the high reflectance (at and near specular) coming from the surface is blocked by the eye pupil. The tumors absorb much more light than healthy tissue because of the intense cellular and vasculature activity in tumorous tissue. Because the near specular reflected light is blocked, the transscleral image of the tumor has more contrast than that obtained with transpupillary illumination and hence allows a better diagnostic of the spatial extent of the tumor (A. Schalenbourg, L. Zografos "Pitfalls in colour photography of choroidal tumours," Eye. 2013, Vol. 27(2): pp. 224-229).

The transscleral methods above are described using one illumination point or sometimes with two illumination points where the two point sources provide illumination simultaneously. Here, by point, we mean "point source like" such as a small area. It can be an area larger than the area given by the diffraction limit.

However, none of the techniques described above provide phase image information in either a quantitative or non-quantitative manner of the inside of eye without the use of a scanning system. This phase contrast is such as but not limited to, the fundus and retina. Accordingly, there is a need to obtain phase information from the biological material above the photoreceptors to obtain improved contrast, improved image resolution and additionally to derive functional information that exist from the large body of research in quantitative phase imaging in biology.

By quantitative phase imaging we mean an imaging technique for which a well-known relationship (such as but not limited to linear or logarithmic) exists between the grayscale pixel value of the camera and the corresponding phase that the physical sample imparted on the light traversing it. Phase unwrapping techniques can be also used to remove the effect of phase periodicity and obtain more detailed images.

In contrast, the absence of an absolute relationship between the grayscale pixel value of the camera and the corresponding phase that the physical sample imparted on the light traversing it is termed as non-quantitative or qualitative phase imaging. An example of qualitative phase imaging is phase gradient contrast and it is given in T. N Ford, K. K Chu and J. Mertz, "Phase-gradient microscopy in thick tissue with oblique back-illumination," Nat. methods, 9, 12 (2012).

Retinal images refinement has been obtained in different ways. One of the main characteristics of human the retina is the presence of cone cells. At high magnifications cone cells appear like bright spots on a dark background allowing for guiding star reconstruction algorithm (N. Meitav and E. N. Ribak, "Estimation of the ocular point spread function by retina modeling", Optics Letter Vol 37 (9) (2012) and N. D. Shemonski, F. A. South, T. Z. Liu, S. G. Adie, P. S. Carney and S. A. Boppart "Computational high-resolution optical imaging of the living human retina" Nature Photonics (2015)). Another method takes advantages of natural movements of the eye (saccades). While most of the studies try to suppress this phenomena that leads to a lower resolution in case of averaging, Meitav and Ribak, used averaging after finding the relative shift of each image N. Meitav and E. N. Ribak "Improving retinal image resolution with iterative weighted shift-and-add" J. Opt. Soc. Am. Vol 28 (7) (2011). This has been done using image correlation and allows to align all the images while performing the average. Due to eye motion, each image presents a different aberrated PSF (point spread function), the resulting averaged image shows an averaged PSF, filtering out the highest order aberrations. One can then obtain a PSF that is much more similar to the diffraction limited one. The effect of eye aberrations can be further decreased by deconvolving the picture with different PSF and estimating the best one. This process has been performed by Hillmann et al. (D. Hillmann, H. Spahr, C. Hain, H. Sudkamp, G. Franke, C. Pflffle, C. Winter, and G. Hittmann "Aberration-free volumetric high-speed imaging of in vivo retina" Scientific reports, Vol. 6 (2016)). In their work deconvolution is obtained with different PSF based on the typical eye aberrations. Entropy is used as a measurement of image quality for estimating the best correction and producing high resolution pictures. Furthermore, the phase and absorption reconstruction using Waller's method (L. Tian and L. Waller, "Quantitative differential phase contrast imaging in an LED array microscope," Opt. Exp. 23, 9, pp. 11394-11403 (2015)) consists already in a deconvolution process. The method can be used to obtain phase and absorption information also in the case of a known or an unknown aberrated pupil (Z. Phillips, M. Chen, L. Waller "Quantitative Phase Microscopy with Simultaneous Aberration Correction" Optics in the Life Science 2017).

High resolution imaging of the living retina is performed by aberration correction. This task is done computationally as presented in U.S. Pat. No. 8,731,272, or using hardware devices. In vivo imaging of the retina is usually performed by a scanning system, U.S. Pat. No. 4,213,678, possibly coupled to adaptive optics, European Pat. No. 1427328 A1, or using a camera flood illumination system, also sometimes coupled to adaptive optics, as for instance in U.S. Pat. Pub. No. 2004/0189941, U.S. Pat. No. 7,364,296.

The resolution in optical imaging of the eye is mostly limited by three factors: pupil's numerical aperture (0.24 maximum (R. K. Wang and V. V. Tuchin, "Advanced Biophotonics: Tissue Optical Sectioning," CRC Press, 2014)), lens' aberrations and intra ocular scattering. Compensation for the last two effects have been proposed leading to the so-called Adaptive Optics Confocal Scanning Laser Ophthalmoscope (AOCSLO) (A. Roorda, F. Romero-Borja, W. Donnelly, H. Queener, T. Hebert, and M. Campbell, "Adaptive optics scanning laser ophthalmoscopy," Opt. Express, vol. 10, pp. 405-412, 2002.)

This system, sometimes coupled with Optical Coherence Tomography (OCT) (E. M. Wells-Gray, R. J. Zawadzki, S. C. Finn, C. Greiner, J. S. Werner, S. S. Choi, N. Doble, "Performance of a combined optical coherence tomography and scanning laser ophthalmoscope with adaptive optics for human retinal imaging applications," Proc. SPIE, vol 9335, pp, 2015), provides a lateral resolution of about 1.5 um, and 2 um axially. This value is limited by the numerical aperture provided by the eye pupil. A wavefront shaping method has been used by Vellekoop and Mosk to perform focusing of light through a highly scattering medium (I. M. Vellekoop, A. Lagendijk and A. P. Mosk, "Exploiting disorder for perfect focusing," Nature Photonics, vol. 4, pp 320-322, 2010). Further works showed how scattering media can be used as optical elements to provide high numerical aperture (NA=0.85) (Y. Choi, T. D. Yang, C. Fang-Yen, P. Kang, K. J. Lee, R R. Dasari, M. S. Feld, and W. Choi, "Overcoming the Diffraction Limit Using Multiple Light Scattering in a Highly Disordered Medium," Phys. Rev. Lett., vol. 107, no. 2, pp. 023902, 2011 and I. N. Papadopoulos, S. Farahi, C. Moser, D. Psaltis, "Increasing the imaging capabilities of multimode fibers by exploiting the properties of highly scattering media," Optics Letters, vol. 38, pp. 2776-2778, 2013). Using the memory effect, it is possible to scan this spot for reconstructing a picture of the scanned object (C.-L. Hsieh, Y. Pu, R. Grange, G. Laporte, and D. Psaltis, "Imaging through turbid layers by scanning the phase conjugated second harmonic radiation from a nanoparticle," Opt. Express 18, 20723-20731 (2010)). Another technique consists in scanning the sample directly with the speckle pattern and reconstructing the original image by a phase retrieval algorithm (X. Yang, Y. Pu, and D. Psaltis, "Imaging blood cells through scattering biological tissue using speckle scanning microscopy," Opt. Express 22, 3405-3413 (2014) and H. Yilmaz, E. G. van Putten, J. Bertolotti, A. Lagendijk, W. L. Vos, and A. P. Mosk, "Speckle correlation resolution enhancement of wide-field fluorescence imaging," Optica 2, 424-429 (2015)).

Accordingly, as discussed above, in the background art of imaging instruments for ophthalmology, the retina is always illuminated by passing through the lens of the eye. Then, the reflected light is again collected via the lens. Also, as discussed above, this presents several drawbacks and complications, and novel and substantially improved methods, systems, and devices for ophthalmology are desired.

SUMMARY OF THE INVENTION

According to one aspect of the present invention, a method for imaging a tissue of an eye is provided. Preferably, the method includes the steps of providing oblique illumination to the eye by a plurality of light emitting areas of a light delivery device, the plurality of light emitting areas being independently controllable and arranged to direct light towards at least one of a retina and an iris of the eye, causing an output beam from light backscattered from the at least one of the retina and the iris by the oblique illumination; and capturing the output beam with an imaging system to provide a sequence of images of a fundus of the eye.

Moreover, the method further preferably includes a step of retrieving a phase and absorption contrast image from the sequence of images of the fundus, and the sequence of images of the fundus of the step of capturing is obtained by sequentially turning on one or more of the plurality of light emitting areas at a time in the step of providing the oblique illumination.

According to another aspect of the present invention, the tissue of the eye is part of a living eye of a human or an animal, and the oblique illumination is at least one of a transpupillary illumination, a transscleral illumination, and a transepidermal illumination. In addition, the light delivery device is configured for at least one of the following illumination modalities, including no contact between the light delivering device and a face of a patient of the eye, the light delivering device is in contact with a skin surrounding the eye, the light delivering device is in contact with a sclera of the eye, and the light delivering device is in contact with a cornea of the eye.

According to still another aspect of the present invention, a system for imaging a tissue of an eye is provided. The system preferably includes a light delivering device having a plurality of light emitting areas, the light emitting areas directed towards the tissue of the eye for providing oblique illumination, an output beam caused by light backscattered off a fundus of the eye of the oblique illumination from the plurality of emitting areas, and an imaging system configured to capture the output beam and to provide a sequence of images of the fundus of the eye.

Moreover, the system further preferably includes a controller configured to individually control the plurality of light emitting areas of light delivering device, to sequentially turn on one of the plurality of light emitter areas at a time, for capturing the sequence of images by the imaging system, and the imaging system is further configured to retrieve a quantitative phase contrast image, a quantitative absorption image, a qualitative phase and absorption image, a qualitative phase contrast image, a qualitative absorption image, a qualitative phase and absorption image, and a dark field image from the fundus of the eye.

According to yet another aspect of the present invention, the imaging system preferably further includes a scanning system and a detector, the scanning system having a collection pupil that is either centered or shifted with respect to a center of a pupil of the eye, and the detector includes at least one of a single pixel detector, a line camera, a two-dimensional multipixel device and a split detector.

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF THE SEVERAL VIEWS OF THE DRAWINGS

The accompanying drawings, which are incorporated herein and constitute part of this specification, illustrate the presently preferred embodiments of the invention, and together with the general description given above and the detailed description given below, serve to explain features of the invention.

FIG. 5 shows the in vivo darkfield imaging of the retina using a modified AOSLO system with offset aperture, image adapted from Toco Y. P. Chui, Dean A. VanNasdale, and Stephen A. Burns, the use of forward scatter to improve retinal vascular imaging with an adaptive optics scanning laser ophthalmoscope, Biomed. Opt. Express 3, 2537-2549 (2012), according to the background art;

FIG. 27 shows a photograph of a subject positioned on an ophthalmic head mount with two prototypes light sources placed on top and bottom of the eye lid respectively. In the image, one LED is switched ON;

FIG. 33A shows the reflectance before running the algorithm, while FIG. 33B the final result. The same profile along one dimension is plotted for low NA in FIG. 33C and for maximum NA (open diaphragm) in FIG. 33D;

FIG. 40C shows a typical transcleral illumination image of a human retina, exhibiting vessel shadows;

Herein, identical reference numerals are used, where possible, to designate identical elements that are common to the figures. Also, the images are simplified for illustration purposes and may not be depicted to scale.

DETAILED DESCRIPTION OF THE SEVERAL EMBODIMENTS

Figure 1:
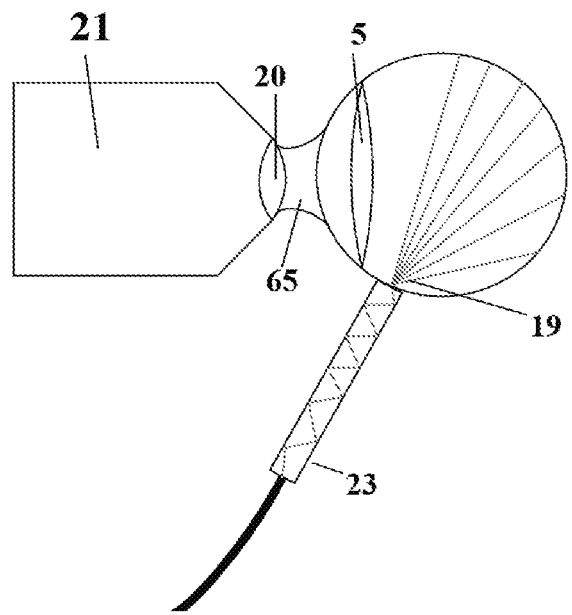
FIG. 1 shows a scheme of the working principle of the system presented in U.S. Pat. No. 7,387,385, U.S. Pat. Pub. No. 2007/0159600 according to the background art. A waveguiding component is put in contact with the sclera to provide illumination. The user has to hold this waveguiding component.

According to one aspect of the present invention, a device for retinal imaging is provided that can establish phase and absorption contrast image thanks to oblique illumination of the retinal layers. According to an aspect of the invention, the device can be used to ex-vivo and in-vivo imaging. In the first part of this section, the ex-vivo implementation is summarized, and the in-vivo implementation is detailed in the second part.

The phase and absorption contrast image can include, but is not limited to a quantitative phase contrast image, a quantitative absorption image, a qualitative phase and absorption image, a qualitative phase contrast image, a qualitative absorption image, a qualitative phase and absorption image, and a dark field image. Also, phase and absorption contrast image can include but is not limited to one dimensional image, two dimensional image, three dimensional image, or multidimensional image.

An ex-vivo sample from the eye can include but is not limited to an entire eye, an untreated piece of an eye, a fixed piece of an eye, a stained piece of an eye, and an in-vitro sample.

Regarding the ex-vivo imaging, instead of using direct illumination of the sample, according to an aspect of the present invention, phase contrast is obtained by oblique illumination generated by scattering in the deep layers of the eye. In a first embodiment, the sample is illuminated with an light source and an oblique angle. In a second embodiment, the source is placed in the same side as the imaging system, making a reflection configuration. In a third embodiment, a scattering layer is placed behind the phase sample to provide a backscattered illumination. In a fourth embodiment, the scattering layer providing the back illumination is the choroid of the eye. In a fifth embodiment, the light source is scattered by a diffusing plate before reaching the sample. In a sixth embodiment a back reflective layer is added below the sample. For the reconstruction process, see below.

A light source can include, but is not limited to a light emitting diode, a super luminescent diode, a quantum dot source, a lamp, a blackbody radiation source, a low temporal coherence source, low spatial coherence source, and a laser source.

Regarding the in-vivo imaging, instead of using direct illumination of the eye fundus, phase contrast is obtained by oblique illumination generated by scattering in the deep layers of the eye. The features of the method, device, system can be simplified in the following categories: illumination type, light delivering device, image acquisition system, reconstruction process.

The illumination types can be presented by the following non-limiting and non-exclusive embodiments:

In a first embodiment, the light is passing through the sclera, the choroid and the retina. The transmitted and scattered light illuminates the fundus. In this variant, no or very little light is entering the pupil-lens. The light delivering device is in contact with the sclera. In other variant, transscleral in combination with transpupillary lighting can be used.

In a second embodiment, the light is passing through the skin layer near the eye, sclera, the choroid and the retina. The transmitted and scattered light illuminates the fundus. In this variant, no or very little light is entering the pupil-lens.

In a third embodiment, light is passing through the pupil, directed to the side of the eye. Here the rays are scattered and reflected towards the fundus.

In a fourth embodiment, light is passing through the pupil and directed on the fundus with a certain angle, generating also angled backscattered light.

In a fifth embodiment, light is passing through the pupil and shined on an area close to the imaged region. Light scatters in the deep layer providing, behind the imaged region, an angled illumination.

In a sixth embodiment, light is passing through the temple. The transmitted and scattered light illuminates the fundus. No light is entering the pupil's lens.

In a seventh embodiment, light is transmitted through the pupil or skin and sclera illuminating directly the imaged area of the retina and not its background, thus providing dark field contrast.

In an eighth embodiment, the wavefront is manipulated before entering in the eye. The feedback light is collected through the lens of the eye. Several schemes are then possible, for example the focusing of light on the fundus to compensate for the scattering to obtain a spot size smaller than the resolution of the eye-pupil (0.24 NA), the focusing being obtained with an iterative process, using the feedback light through the eye-pupil as criterion of optimization, and also the scanning of the eye's fundus by using a well-known memory effect in scattering media by adding a phase gradient to the wavefront. The scanning pattern can include either an optimized focus spot or a speckle pattern.

Once the data of the scan is recorded, it is processed with a phase retrieval algorithm or other digital means to reconstruct a super resolved image, i.e. having the resolution of the illumination speckle pattern.

The light delivering device, according to an aspect of the present invention, can be designed for contact and non-contact. The light delivery device for contact is presented in the following embodiments:

The light delivering device is made of a flexible electronic circuit that integrates the light emitting device and the electronic wires that brings the driving signals for the light delivering devices.

The light delivering device is in contact with the skin or sclera and the light delivering device in contact with the skin has a removable protection patch (one for each patient).

The parts that are in contact with a face of a patient whose eye is analyzed can include but is not limited to a head holder, a chin holder and a light delivering device are covered with a removable disposable part. A removable part can include but is not limited to a layer of paper, a stack of paper layers, a polymeric layer.

The shape of the flexible electronic circuit of the light delivering device is designed in an ergonomic way.

The flexible electronic circuit—patch is held with a head-mounted frame (e.g. a glass' frame) placed on the subject.

An absorptive or reflecting layer placed on the back of the illumination device for suppressing backscattered light.

The light delivering device for non-contact illumination is presented in the following embodiments:

The contactless light delivering device is made of point sources which are imaged on the illumination surface (cornea, sclera or skin).

The contactless light delivering device consists in a circular source whose light is shined on the illumination surface (cornea, sclera or skin).

The contactless light delivering device consists in an annular whose light is shined on the illumination surface (cornea, sclera or skin).

Illumination is provided thanks to a single or a combination of light sources in the wavelength range of 400 nm to 1200 nm such as but not limited to: pulsed or continuous laser source, light emitting diode, super luminescent diode, quantum dot source, a lamp, a black body radiation source, and a laser source. Light is delivered by placing the source in direct contact with the tissue (sclera or skin) or guided from the source to the tissue or imaging the source on the illumination surface (cornea, sclera or skin). Waveguiding components include but are not limited to: multimode fibers, capillary waveguides, lensed multimode fibers, single mode fibers and photonic crystal fibers. Light beam can be converging, diverging or collimated, depending on the chosen illumination technique. Light can be but not limited to linearly polarized, circularly polarized, non-polarized (meaning that does not presents any known preferential polarization), and a mixture of different polarizations.

In Fourier domain, oblique illumination with a plane wave is equivalent to a shift towards higher spatial frequencies, meaning a higher spatial resolution. In addition, shining light on the fundus with higher angles will also produce a more oblique back illumination, providing higher contrast.

The image acquisition process is different depending on the required imaging modality: dark field or phase/absorption. For dark field, imaging can be performed with just one illumination point without image processing. A wider field of view is obtained by stitching together images obtained for different imaging areas.

For the image acquisition system, the following operational steps or scheme can be performed: An image of the retina is formed on the camera thanks to a series of lenses and mirrors. A lens or a mirror is translated to change the focal plane in the retina. A tunable lens that is used to change the focal plane in the retina. A cylindrical lens is rotated and translated to compensate for eye's astigmatism. Two independent cylindrical lenses are translated to compensate for eye's astigmatism. Patient's prescription glasses are used to compensate for eye aberrations. A deformable mirror is used to compensate for eye's aberration. A wavefront sensor is conjugated to the pupil's plane to measure eye's aberrations. A camera is conjugated to the pupil's plane to measure the illumination function. A diaphragm is conjugated to the retina to select a small area of the retina for measuring the illumination function. A camera is conjugated to the cornea to observe when the patient's eye is at the right position. Moreover, polarization optics can be used to stop light's backreflection at the different surfaces.

For the reconstruction, the following operational steps can be performed: The illumination profile of the retina (backscattered light) is not an even function in the range of collection NA. The light used for illumination passes through the retina and its phase and intensity is affected by its optical properties. The modulated light is recorded on a camera for different illumination functions. Pictures are processed together to reconstruct the phase and absorption image. The image quality is improved by increasing resolution and contrast via image processing. Anatomical features are extracted and analyzed to detect possible abnormalities.

Phase imaging requires at least two pictures captured with two different illumination points. By using a reconstruction algorithm, it is possible to obtain a qualitative or quantitative phase image. Such reconstruction algorithms known in the art can be, but not limited to, those described in L. Tian and L. Waller, "Quantitative differential phase contrast imaging in an LED array microscope," Opt. Exp. 23, 9, 11394-11403 (2015), in Z. Phillips, M. Chen, L. Waller "Quantitative Phase Microscopy with Simultaneous Aberration Correction" Optics in the Life Science 2017 or in Int. Pat. Pub. No. WO 2015/179452, S. B. Mehta and C. J. R. Sheppard, "Quantitative phase-gradient imaging at high resolution with asymmetric illumination-based differential phase contrast," Opt. Lett. 34, 13, 1924-1926 (2009). The proposed illumination schemes, discussed as exemplary embodiments, can be combined to record the images to process.

Phase imaging is based on the interference of the beam with itself due to phase difference in the object plane. This interference, in the case of a non-even illumination results in a modulation of the intensity at the camera layer. By recording two pictures with opposite illumination profile ($S_1(u)=S_2(-u)$) and subtracting their intensity the background signal is removed, leaving only the phase information. One obtains an image which is the differential phase contrast (Z. Liu, S. Liu and L. Waller "Real-time brightfield, darkfield, and phase contrast imaging in a light emitting diode array microscope," J. of Biomed. Opt. 19, 10, 106002 (2014), T. N Ford, K. K Chu and J. Mertz, "Phase-gradient microscopy in thick tissue with oblique back-illumination,"

Figure 3:
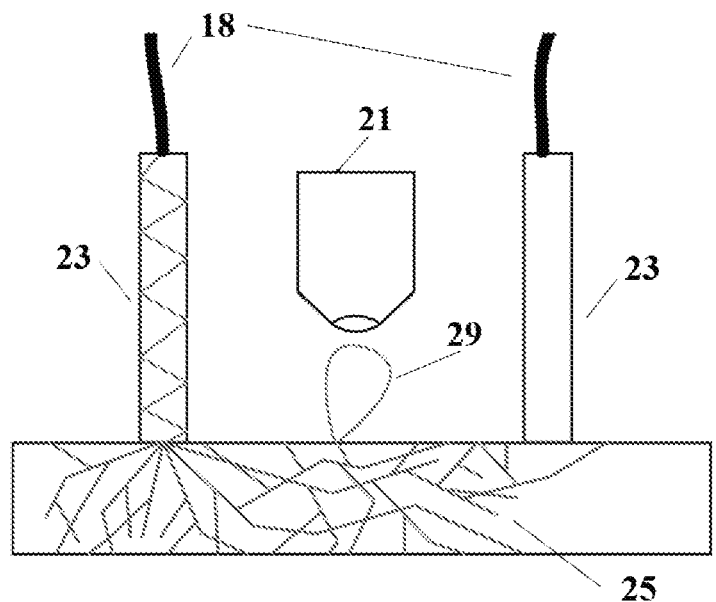
FIG. 3 shows an illumination system presented in T. N Ford, K. K Chu and J. Mertz, "Phase-gradient microscopy in thick tissue with oblique back-illumination," according to the background art, Nat. methods, 9, 12 (2012) and Int. Pat. Pub. No. WO 2013/148360. Light is guided and delivered at the surface of the scattering media. Here, thanks to scattering, some of the light travels back up to the surface, emerging with an asymmetric angle distribution. A second waveguiding component is present for providing the symmetrical illumination.
Figure 4A:
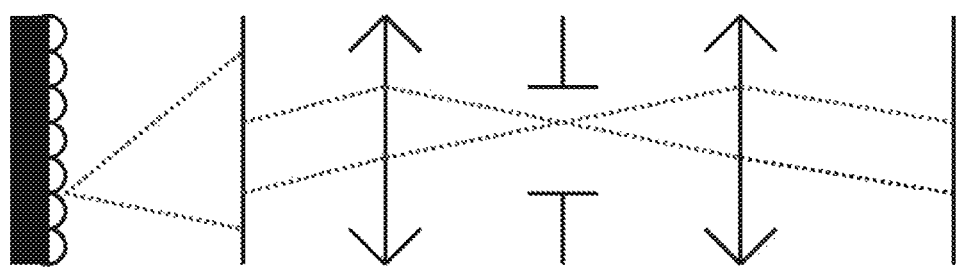
FIGS. 4A and 4B schematically show two different representations of a transmission microscopy phase imaging method using incoherent darkfield illumination, presented in L. Tian and L. Waller, "Quantitative differential phase contrast imaging in an LED array microscope," Opt. Exp. 23, 9, 11394-11403 (2015), according to the background art.
Figure 4B:
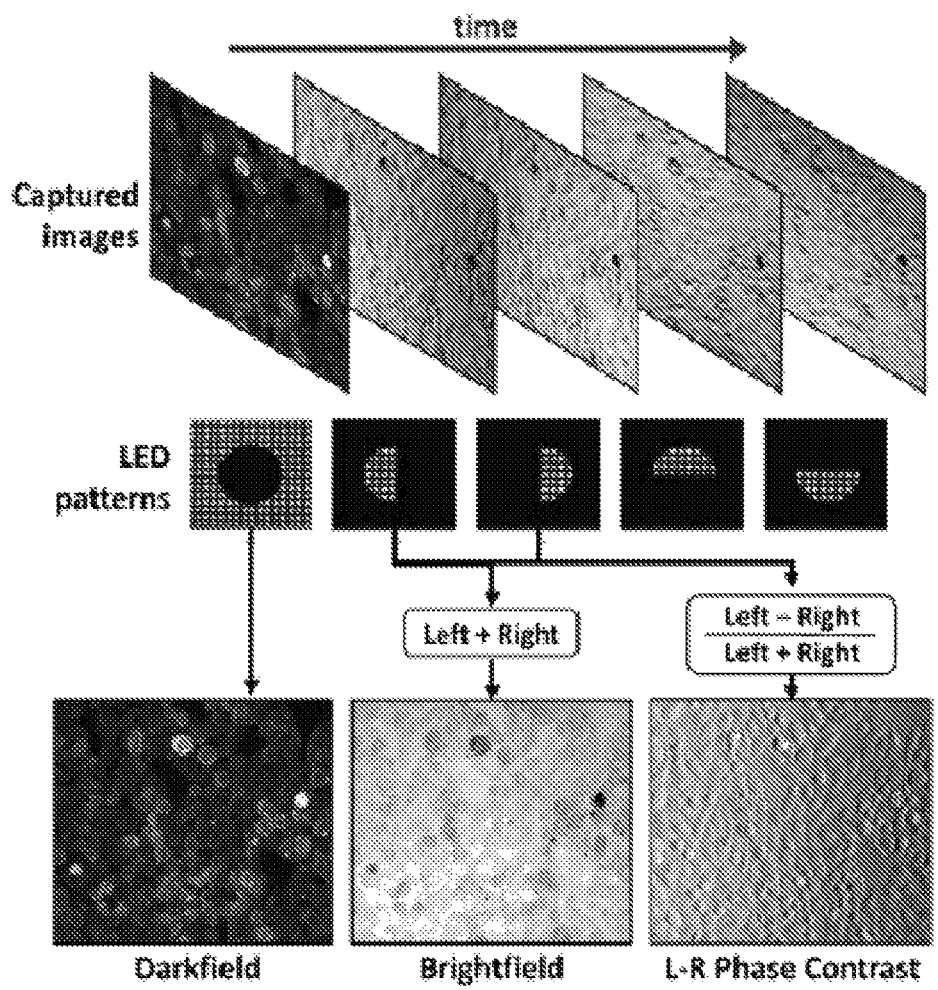
Figure 6:
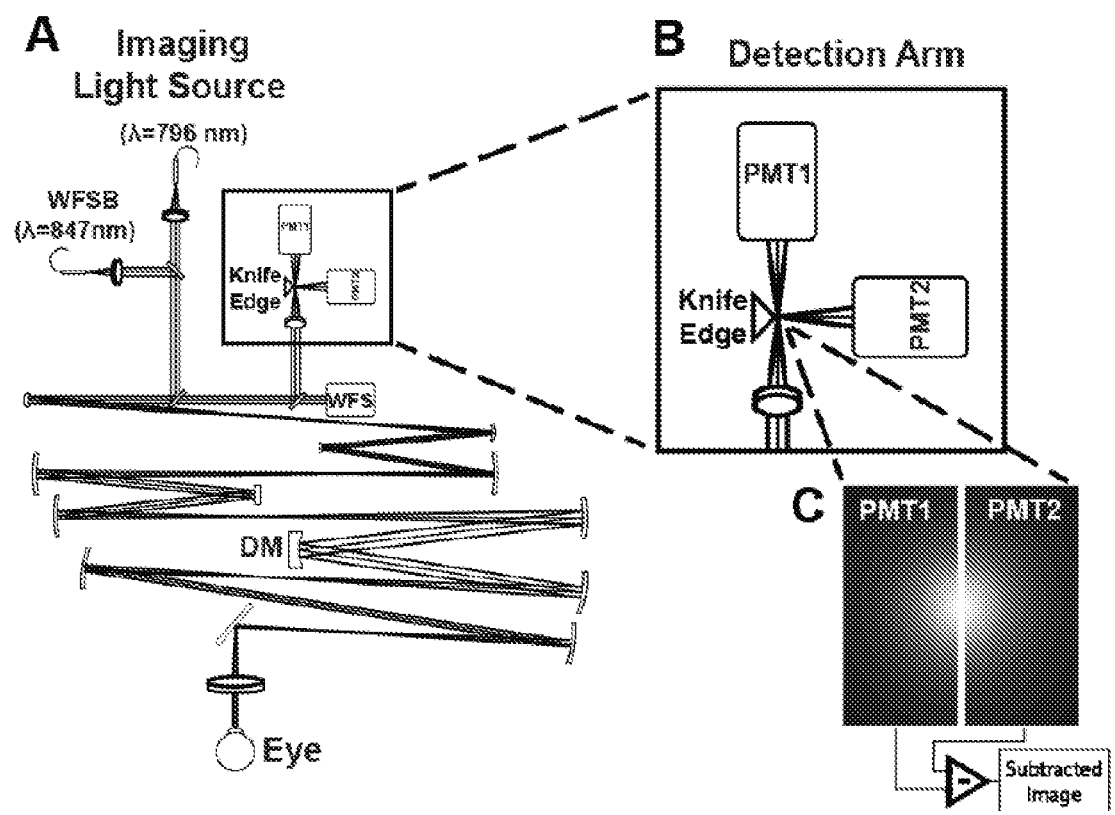
FIG. 6 shows in vivo darkfield imaging of the retina using a modified AOSLO system with split detector, image adapted from A. Guevara-Torres, D. R. Williams, and J. B. Schallek, Imaging translucent cell bodies in the living mouse retina without contrast agents, Biomed. Opt. Express 6, 2106-2119 (2015), according to the background art.
Figure 7:
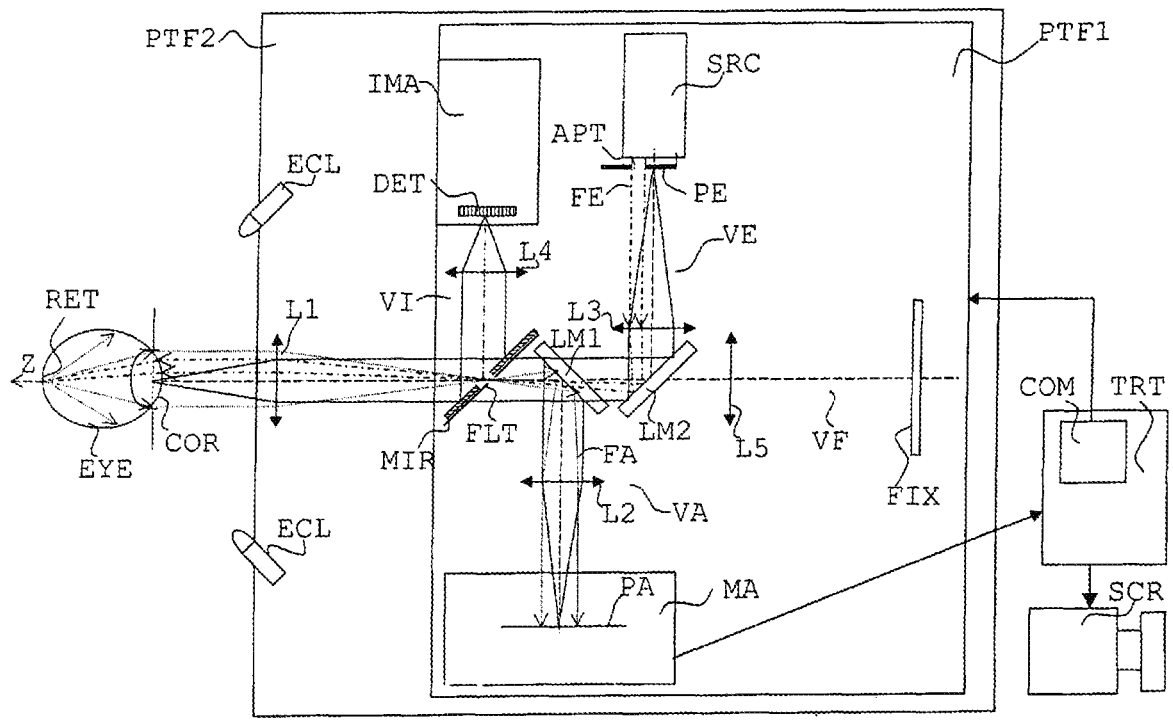
FIG. 7 shows a flood illumination adaptive optic system with transpupillary illumination, as shown in U.S. Pat. Pub. No. 2004/0189941, according to the background art.

Nat. methods, 9, 12 (2012)). The principle is shown in the representations of FIGS. 3, 4A and 4B.

If the two complementary illumination angles images are I0 and I1, the differential phase contrast image is computed by $$Idiff=(I0-I1)/(I0+I1) \quad (1)$$

The intensity values in the image are related to the phase gradient in the image plane. Since this technique requires the illumination beam to be transmitted through the sample it appeared to be impossible for thick biological media.

Figure 34:
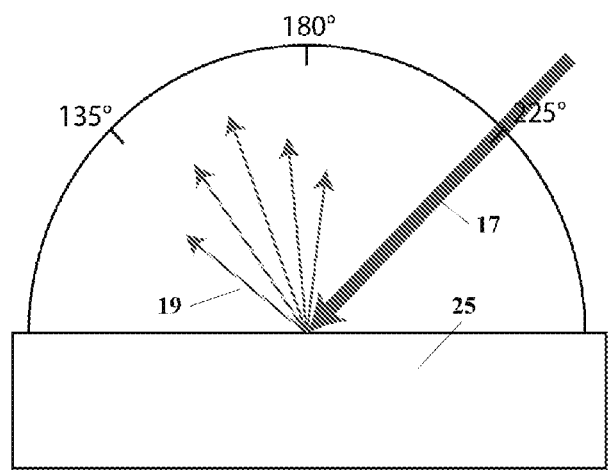
FIG. 34 is a schematic representation of the backscattered light's angular distribution with oblique illumination, according to an aspect of the present invention.
Figure 35:
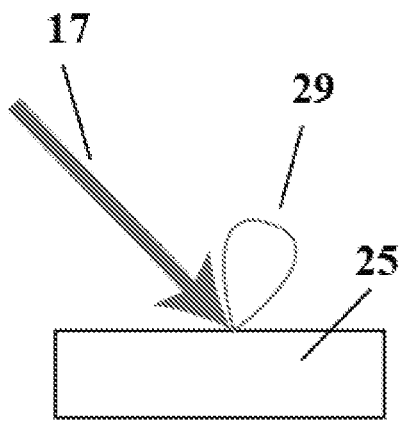
FIG. 35 is a schematic representation of how the beam is scattered at the surface of a scattering media, according to an aspect of the present invention. The case of oblique illumination is represented, showing also an anisotropic scattering (the scattered beam is not symmetric respect the perpendicular to the surface)
Figure 36:
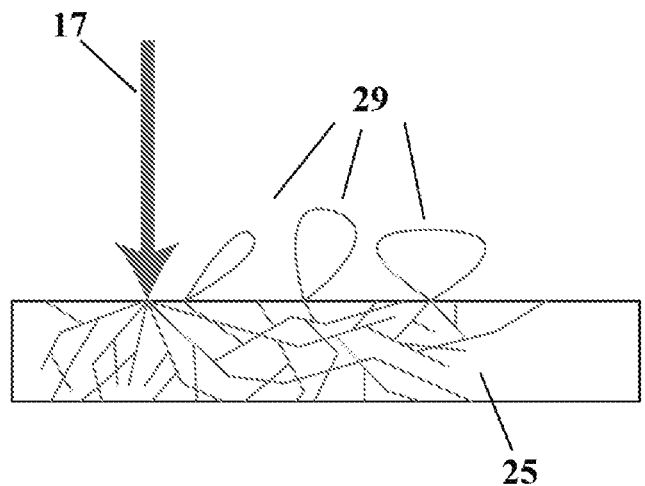
FIG. 36 shows a schematic representation of angular distribution of the emerging beams at different distances from the illuminating beam, according to an aspect of the present invention. The more the distance increases the more the emerging beam will look like a Lambertian distribution.
Figure 37:
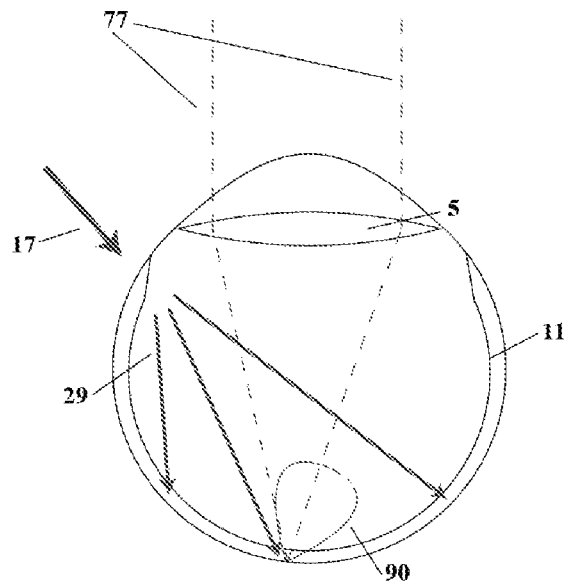
FIG. 37 shows a schematic representation of an illumination beam is shined on the eye tissue, according to an aspect of the present invention. After travelling through the different layers it emerges as scattered beam. After passing through the transparent retinal layers it is scattered back by deeper tissues (e.g. choroid). The backscattered light presents an oblique mean distribution and, passing again through the retina, the cells contained in the retina alters the phase of the light passing through it. After travelling through the eye it is collected by the eye lens and sent outside as a collimated beam.

It has been shown how the properties of a scattering media, like a biological tissue, can be used for providing a sort of back illumination of the sample (T. N Ford, K. K Chu and J. Mertz, "Phase-gradient microscopy in thick tissue with oblique back-illumination," Nat. methods, 9, 12 (2012)). Indeed, if a beam of light is shined perpendicularly on a scattering media, the backscattered light will show different angular distribution, depending on the distance away from the beam incident position, see in FIG. 3. This uneven angle distribution results in a tilted averaged illumination, which can be used for providing oblique illumination. A similar effect can be observed if the shining beam is not perpendicular to the surface, and the backscattered beam will present directionality, as shown in FIGS. 34 and 35.

This effect can be used in eyes such as but not limited to the human eye: when light is shined on the fundus with a certain angle, (e.g. when passing through the sclera) it travels through the transparent retinal layers and scatters in the deeper layers (e.g. pigmented epithelium and choroid). Here light scatters back, maintaining an oblique direction, and passing through the upper layers of the retina it is affected by retinal absorption and phase.

By acquiring pictures sequentially for at least two different complementary illumination angles (e.g +90 and −90 degrees), it is possible to use phase gradient imaging algorithm (T. N Ford, K. K Chu and J. Mertz, "Phase-gradient microscopy in thick tissue with oblique back-illumination," Nat. methods, 9, 12 (2012), S. B. Mehta and C. J. R. Sheppard, "Quantitative phase-gradient imaging at high resolution with asymmetric illumination-based differential phase contrast," Opt. Lett. 34, 13, 1924-1926 (2009), L. Tian and L. Waller, "Quantitative differential phase contrast imaging in an LED array microscope," Opt. Exp. 23, 9, 11394-11403 (2015), see e.g. FIG. 4) or a Fourier ptychography algorithm (Int. Pat. Pub. No. 2015/179452, G. Zheng, R. Horstmeyer, and C. Yang, "Wide-field, high-resolution Fourier ptychographic microscopy") and reconstruct a qualitative or quantitative phase gradient image. This reconstruction process can then be generalized to any kind of illumination introducing the transfer functions of phase and absorption already introduced by Tian and Waller. Indeed, the intensity on the camera can be written as:

$$\tilde{I}_1 = B_1 \delta + H_1 \tilde{\mu} + G_1 \tilde{\phi} \quad (2)$$

Figure 40A:
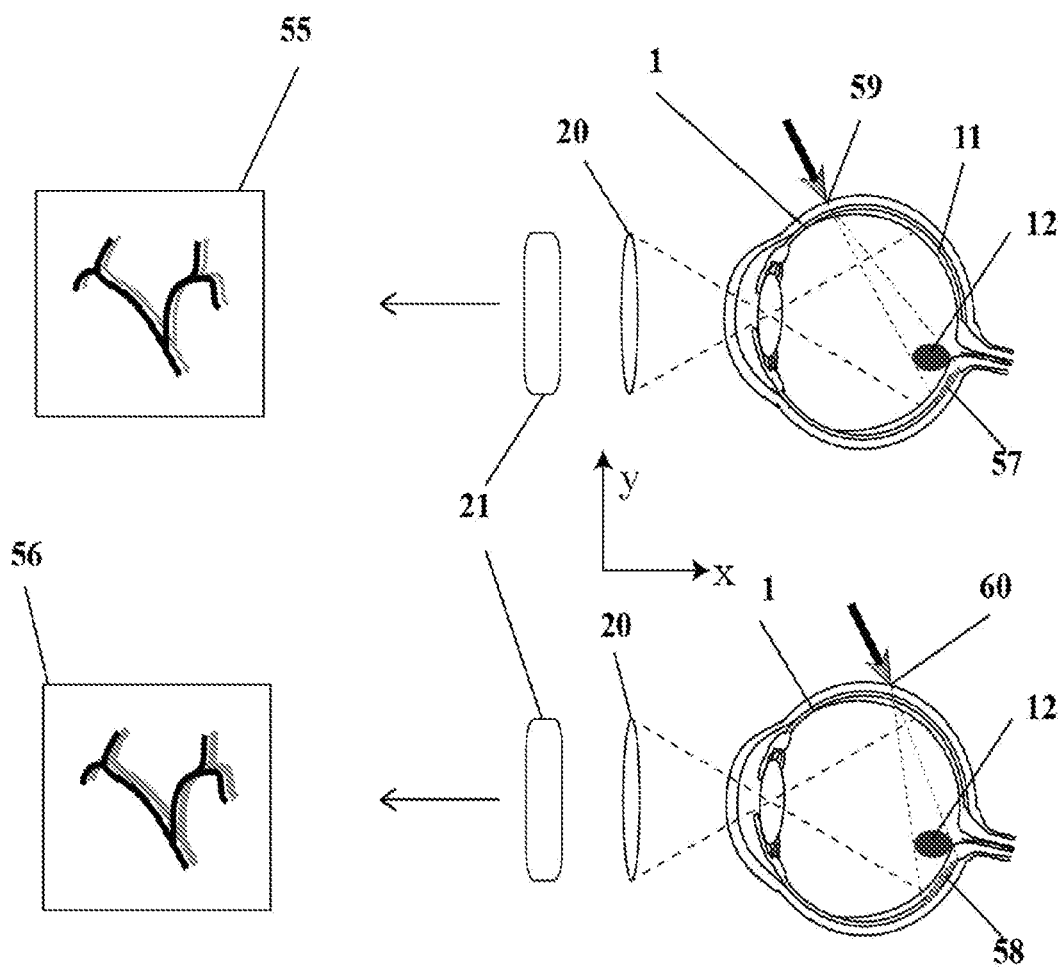
FIGS. 40A, 40B, and 40C show representations that illustrate a method for determining the angular spectrum of an illumination point. For every illumination point, a different shadow is cast off the vessels. The spatial frequency spectrum of the illumination can be determined by using the image of the shadows obtained through the eye lens. The knowledge of the spatial frequency spectrum of each illumination point is then used in the phase retrieval algorithm to provide a quantitative phase image. In addition, the aberration of the eye-lens system is also inferred by the iterative algorithm. This works because there are multiple presentations of the shadows. The more images of shadows at different angles, the more precise the phase image and aberration correction. The principle or method is illustrated for two different illumination points as shown in FIGS. 40A and 40B.
Figure 40B:
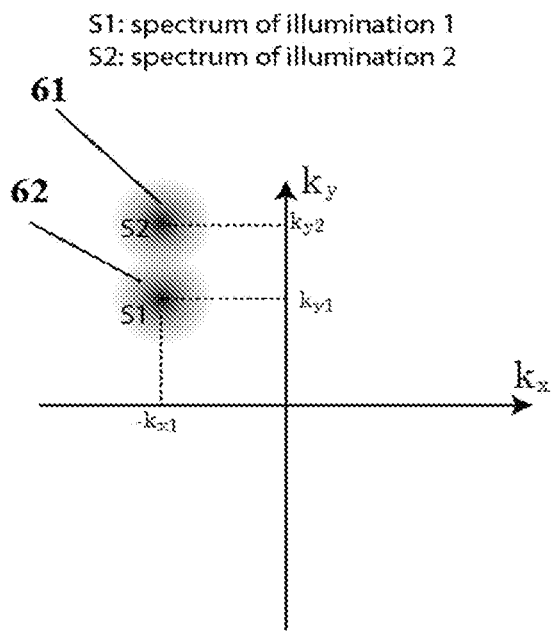
Figure 40C:
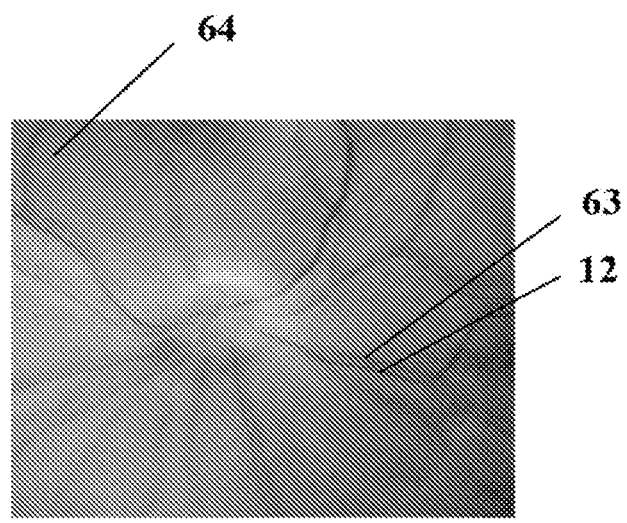
Figure 41:
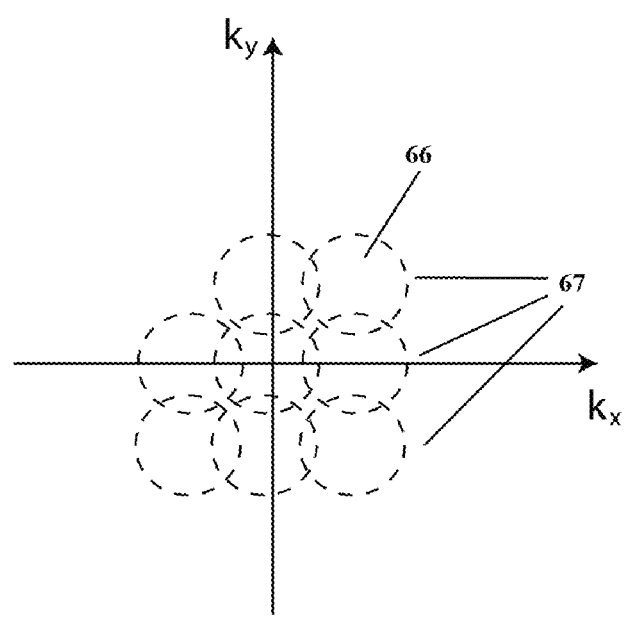
FIG. 41 is a schematic representation showing the stitching different pictures in the Fourier space, according to an aspect of the present invention. Since tilted illumination is equivalent to a shift in Fourier space, stitching, in Fourier domain, pictures with different illumination angles is equivalent to obtaining a single picture with a larger Fourier domain. This results in a higher resolution image.
Figure 49:
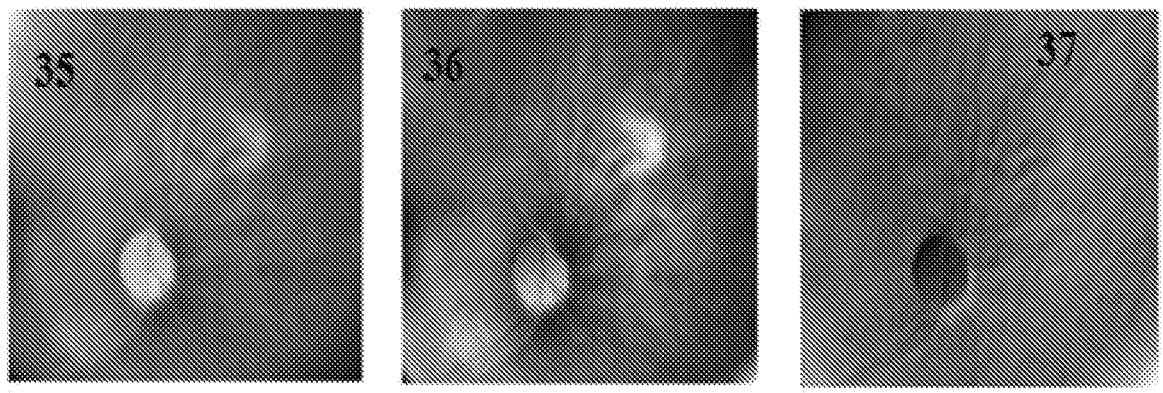
FIG. 49 shows on the left side a picture taken with the transepidermal method with a bottom center point of illumination, in the center a picture taken with the transepidermal method with a bottom left point of illumination, and on the right side the difference of the two showing the phase contrast.

With δ Dirac's delta function and $B_1$, $H_1$ and $G_1$ transfer functions dependant only on S. Since if S is known the only unknown are μ and φ, by acquiring at least two pictures it is possible to obtain the two unknown functions. FIG. 49 illustrates the principle for two different illumination points. The human in-vivo fundus image is taken with transscleral illumination. The shadow in FIG. 40 exhibits an effect of "twin" image for the vessels' tree, as also illustrated in images 55 and 56, due to the almost transparent layer between the vessels and the layer where the shadows are cast.

Next, some details to the mathematical background for the aspects of the present invention is given. When an image $I_1$ and a second picture $I_2$ are acquired with two different illumination pattern they could be renormalized using different methods, such as but not limited to:

$$N_1\{I_1\} = \frac{I_1}{I_1 + I_2} \quad (3)$$

$$N_2\{I_1\} = \frac{I_1}{\text{Low}\{I_1\}} \quad (4)$$

$$N_3\{I_1\} = \frac{I_1 - \text{Low}\{I_1\}}{I_1} \quad (5)$$

Where $N_i\{\sim\}$ is the i-th renormalization method Low $\{\sim\}$ is a 2D lowpass filter. Together with that it is convenient in many cases also to subtract the resulting image with its average, removing the zero component in the Fourier space.

A normalization method can include but is not limited to the relationship defined in $N_1\{\sim\}$, the relationship defined in $N_2\{\sim\}$ and the relationship defined in $N_3\{\sim\}$.

Regarding phase and absorption reconstruction, from the study of Tian and Waller (L. Tian and L. Waller, "Quantitative differential phase contrast imaging in an LED array microscope," Opt. Exp. 23, 9, 11394-11403 (2015)) we can write the image in Fourier as:

$$\tilde{I}_1 = B_1 \delta + H_1 \tilde{\mu} + G_1 \tilde{\phi} \quad (6)$$

Where $\tilde{\mu}$ and $\tilde{\phi}$ are the Fourier transform of the absorption and phase profile respectively and $H_1$, $G_1$ and $B_1$ are functions dependent to the illumination function and pupil's aberration in measurement 1. From this we can obtain the two profiles as:

$$\tilde{\phi} = \frac{H_2 \tilde{I}_1 - H_1 \tilde{I}_2 + (B_2 H_1 - B_1 H_2)\delta}{H_2 G_1 - H_1 G_2} \quad (7)$$

$$\tilde{\mu} = \frac{G_2 \tilde{I}_1 - G_1 \tilde{I}_2 + (B_2 G_1 - B_1 G_2)\delta}{H_2 G_1 - H_1 G_2} \quad (8)$$

If more than 2 images are acquired we can define a phase DPC image between the image i and image j as:

$$P_{ij} = H_j I_i - H_i I_j + (B_j H_i - B_i H_j)\delta \quad (9)$$

And for absorption as:

$$A_{ij} = G_j \tilde{I}_i - G_i \tilde{I}_j + (B_j G_i - B_i G_j)\delta \quad (10)$$

And the transfer function as:

$$T_{ij} = H_j G_i - H_i G_j \quad (11)$$

Thanks to that is possible to reconstruct using different DPC images, for example using Weiner filtering as:

$$\tilde{\phi} = \sum \frac{T_{ij}^* P_{ij}}{|T_{ij}|^2} \quad (12)$$

$$\tilde{\mu} = \sum \frac{T_{ij}^* A_{ij}}{|T_{ij}|^2} \quad (13)$$

Regarding the illumination function estimation, three different variants are presented. In the flat approximation method, as previously mentioned reconstruction is possible only by knowing the different H and G. That can be obtained from the studies of Waller and Tian by knowing the pupil function (aberration) and the illumination profile S.

The method for obtaining phase and absorption using the DPC images obtained by equations (9) and (10) and with the transfer function (11) is what here is called Modified Waller Method (MWM). In the special case where $B_1=B_2$, $H_1=H_2$ and $G_1=-G_2$ it can be simplified in the Waller Method (WM) for obtaining phase with DPC image as:

$$P_{ij}=I_i-I_j \quad (14)$$

and transfer function $$T_{ij}=2G_i \quad (15)$$

Each one of these methods requires a deconvolution step in with the DPC image is deconvolved with the transfer function. This can be performed with different methods such as but not limited to: direct inversion, Weiner filtering, conjugate gradient minimization, maximum likelihood method, blind deconvolution methods.

These methods for retrieving phase and absorption are here called "phase and absorption retrieval algorithm." A phase and absorption retrieval algorithm can include, but is not limited to: a Waller method with or without renormalization, a Waller modified method with or without renormalization, and a phase retrieval algorithm.

The first method consist in approximates $S(u)=h(au_x+bu_y)$, where $h(u_i)$ represents the Heaviside function dependent on the only coordinate $u_i$, and a and b are two coefficients that are chosen to determine which half spaced will be equal to 1. This method completely ignores the angular distribution of the backscattered light, allowing for the reconstruction without any other study on the illuminated surfaces. Reconstruction is then provided by mean of, but not limited to, inverse filtering, least square filter, constrained least-square filter, Tikhonov regularization, blind deconvolution, iterative filters and it can be applied both in spatial or Fourier domain. The image of FIG. 49 is obtained with this approximation and then reconstructing the phase image with Tikhonov regularization.

Regarding the ramp approximation method, this method is similar to the one obtained before, but, instead of using an Heaviside approximation, the illumination function is chosen as $S(u)=au_x+bu_y+q$. With a, b and q arbitrary values. Then the images can be reconstructed with the same methods as proposed in the flat approximation method.

Figure 51:
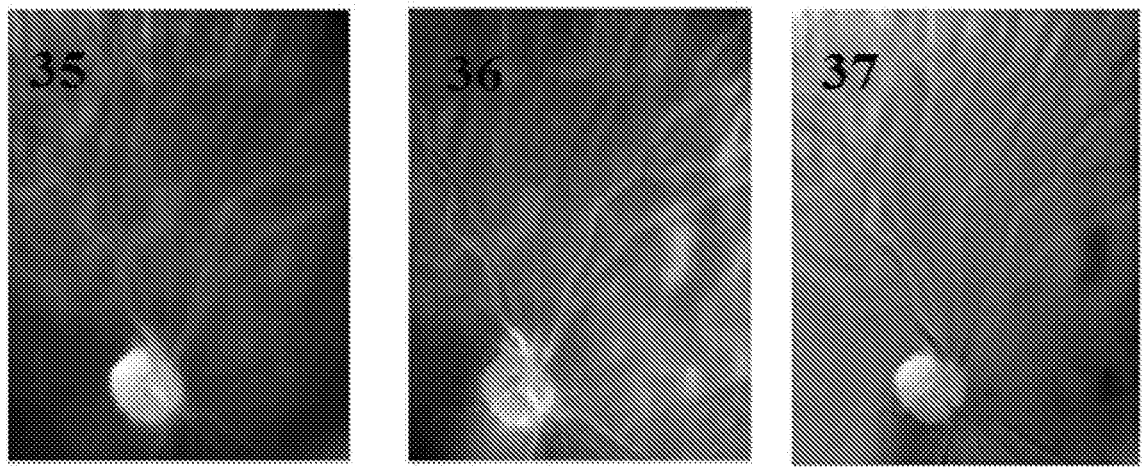
FIG. 51 shows on the left side a picture taken with the transepidermal method with a bottom right point of illumination, in the center a picture taken with the transepidermal method with a bottom left point of illumination, and on the right side difference of the two showing the phase contrast.

Next, regarding the angular scattering information method, this method is based on a precise knowledge of the function S(u). This function is obtained with, but not limited to, Monte-Carlo scattering simulations or experimental measurements. Experimental results can be obtained, but not limited to, a camera conjugated to the pupil's plane. Reconstruction can the obtained by using the same techniques as mentioned in method 1. The image shown in FIG. 51 is obtained with the function S(u) obtained from Monte-Carlo simulations and then reconstructing the phase image with Tikhonov regularization. The parameters used for the simulations were obtained from Rovati et al. (L. Rovati, S. Cattini, N. Zambelli, F. Viola, and G. Staurenghi, "In-vivo diffusing-wave-spectroscopy measurements of the ocular fundus", Optics Express Vol. 15, Issue 7, pp. 4030-4038 (2007)) and from Curcio et al. (C. A. Curcio, J. D. Messinger, K. R. Sloan, A. Mitra, G. McGwin, and R. F. Spaide, "Human Chorioretinal Layer Thicknesses Measured in Macula-wide, High-Resolution Histologic Sections", Invest Ophthalmol Vis Sci. 2011 June; 52(7): 3943-3954.

After image reconstruction, resolution is improved by means of, but not limited to, Meitav's or Shemonski's guiding star method, Meitav's shift and add method, Hillman's deconvolution-entropy method, blind deconvolution algorithm or iterative filters. In case of guiding star algorithm the deconvolving function is firstly estimated at the photoreceptors layer by physical focusing. Successively the phase retinal layer is set in focus, images are acquired and the same filter is applied to improve image quality. Filters can be applied on either the raw image or the DPC ($I_{DPC}$) image.

Image quality can also be improved in the reconstruction process. Indeed, if the aberrations at the pupil plane are known the reconstruction restores the original image. If the aberrations are not known, it is still possible to estimate them using a blind-deconvolution approach, as in Phillips (Z. Phillips, M. Chen, L. Waller "Quantitative Phase Microscopy with Simultaneous Aberration Correction" Optics in the Life Science 2017).

Once the phase image has been extracted, an improved pattern recognition algorithm can be run for features extraction. Features extraction is meant to work on retinal features such as, but not limited to, cells, nuclei and microvasculature present in the different retinal layers, for example inner limiting membrane (ILM), retinal nerve fiber layer (RNFL), ganglion cell layer (GCL), inner plexiform layer (IPL), inner nuclear layer (INL), outer plexiform layer (OPL), outer nuclear layer (ONL), external limiting membrane (ELM).

Features extraction is performed with, but not limited to edge detection, corner detection, blob detection, ridge detection, scale-invariant feature transform, Hough transform, for instance based on a deep learning software. In such case, the deep learning software can be trained with pathologic and nonpathologic images (in vivo or ex vivo). Furthermore, the features extraction can be applied to medical information extraction in order to help the clinician analyzing the data.

Regarding the measurements of the illumination function, the illumination function can be estimated by placing a camera in a plane that is conjugate to the pupil's plane in case of curved surface (as in the case of the eye) or to the Fourier plane if the sample surface is flat (as in the case of a flat mounted ex-vivo sample). A diaphragm in a plane conjugate to the sample's plane allows for a better selection of the scattering profile. Indeed, the measured illumination function is averaged over the samples area but, thanks to the diaphragm, this area can be limited and the illumination function can be measured locally. Furthermore a small aperture allows approximating a curved surface as locally flat. Under this consideration there is no more difference between placing the camera at the pupil or at the Fourier plane.

Due to this configuration, the image obtained at the pupil camera is the illumination function averaged over the area limited by the diaphragm aperture. If the illumination function needs to be measured pointwise over different areas of the sample the aperture can be replaced by a lens array. In this configuration, each lens creates the image on the camera of the local illumination function.

Regarding aberration measurement, a limiting factor in the image quality is given by optical aberrations. They can be due to eye's aberration and aberrations of the optical system. Aberrations usually produce a dumping of high frequencies, resulting in a poorer image resolution. In order to compensate for this effect, for example by physical correction or post processing, a wavefront sensor can be part of the system. Many different devices can be used to perform this task, but the main ones used are Shack-Hartmann wavefront sensor and Tscherning wavefront sensor.

In both cases light is sent to the retina and a camera is conjugated to this plane. In the Shack Hartmann case light is sent in order to produce a point, while for Tscheming a pattern similar to a grid of points is imaged on the retina. In the Shack Hartmann a lenses array is then placed in a plane conjugated to the pupil in order to produce several images of the same point on the camera. Since the lens array is conjugated to the pupil plane the image of each spot is translated from the center of the lens of a distance proportional to the local slope of the wavefront. In this way it is possible to reconstruct the wavefront by measuring the spot field. The Tschering wavefront sensor performs the same measurement but producing the spotfield directly on the retina.

Because such a system requires illumination of the retina this light could disturb the retinal image used for reconstruction when the two are used at the same time. Because of that it is convenient to use different wavelengths: one for illumination and the other for wavefront sensing. Filters and dichroic mirrors are then used to avoid light of one system to enter the other one.

Regarding physical aberration correction, aberrations can be compensated in post-processing but, if the dumping effect is too strong, the dynamic range of the camera is not enough to record the information. It is then more convenient physically compensate the effect of aberrations when eye aberrations are too strong. The physical correction can be performed in different ways.

Changing the focal distance of the method, system, and device is useful both in case of eye defocus (myopia/hyperopia) and in the case in which a change of the focal plane is required for example but not limited to the performance of a stack of different planes. This task can be performed in different ways, for example but not limited to translation of the focusing element (lens or curved mirror), translation of mirrors for increasing the path length (badal system), change of focal distance in a tunable lens, change in a deformable mirror.

Furthermore, myopia/hyperopia of a patient can be corrected in the measurement using prescription glasses or contact lenses of the patient.

Another common aberration in human eyes is due to astigmatism. This consists in a difference in focal distance of the lens along two different axes. Because of that astigmatism can be compensated by using, for example, translation of two independent cylindrical lenses, a deformable mirror, prescription glasses or contact lenses of the patient.

Figure 48:
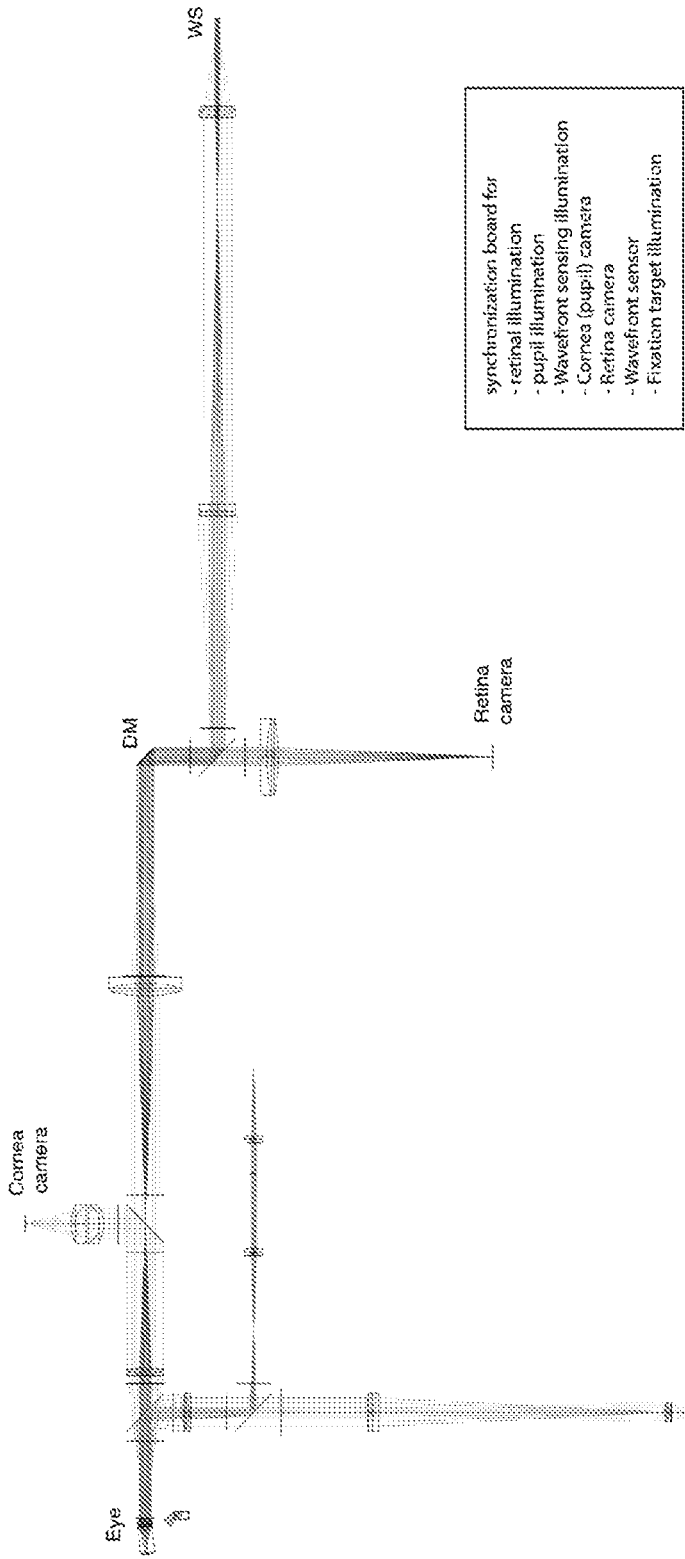
FIG. 48 shows a schematic representation of an example of an optical system designed with an adaptive optics loop to correct for the aberrations of the eye, according to an aspect of the present invention. It integrates a wavefront sensor (WFS) and a deformable mirror (DM)

Referring to FIG. 48, both low and higher order aberrations can be compensated by placing a deformable mirror in a plane conjugate to the pupil's plane. This configuration is more robust if coupled with a wavefront sensor in which the sensor is placed after the deformable mirror. In this way, the wavefront sensor can be used in a closed loop with the deformable mirror to compensate for aberrations.

Moreover, dark-field illumination can be used in the present method, system, and device. With the dark-field illumination, an illumination method is used that employs for illumination a range of illumination angles that is different from the range of collection. In this way transscleral illumination, associated with transpupillary collection, is considered a dark-field illumination.

When light is incident on the fundus, it is scattered by many different layers. The first retinal layers provide relatively intense backscattering. By using different angles for illumination and collection, most of this light scattered by the first retinal layers will be not collected by the pupil. Deeper layers scatter light as well as seen in OCT images or de-centered collection (T. Y. P. Chui, D. A. VanNasdale, and S. A. Burns, "The use of forward scatter to improve retinal vascular imaging with an adaptive optics scanning laser ophthalmoscope," Biomed. Opt. Exp. 3, 10, 2537-2549 (2012), an article in which dark field illumination through the pupil, in illumination and collection, is used to observe retinal and choroidal microvasculature.

Figure 12A:
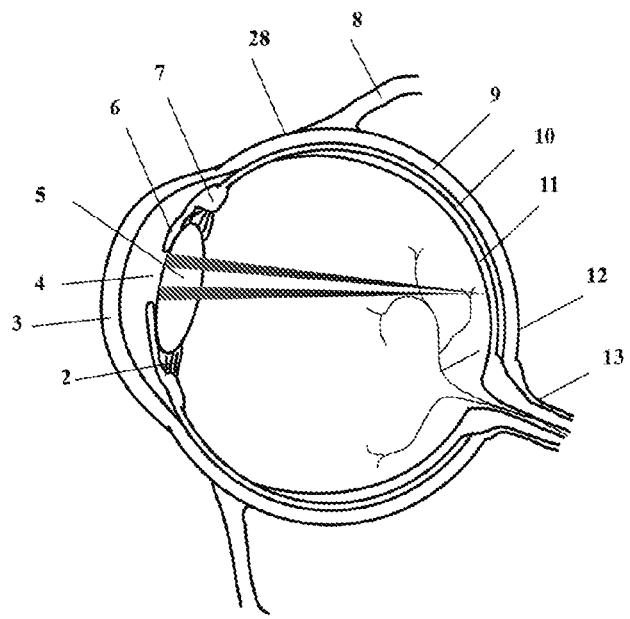
FIG. 12A schematically shows pupillary darkfield illumination according to an aspect of the present invention. Light is shined on the extremity of the pupil (in a single point or in annular shape. Light is illuminating the upper layer of the retina without illuminating the background.
Figure 12B:
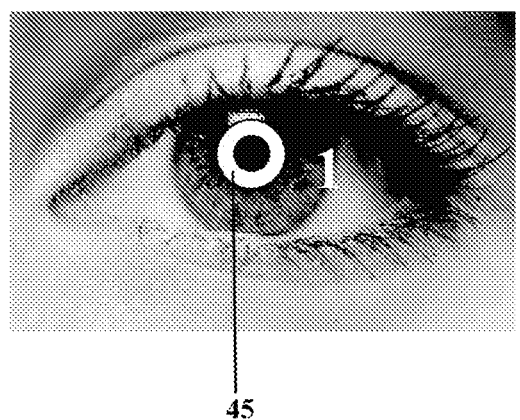
FIG. 12B schematically shows pupillary darkfield illumination according to an aspect of the present invention. The light pattern can be an annulus or a restricted portion of the annulus.
Figure 13:
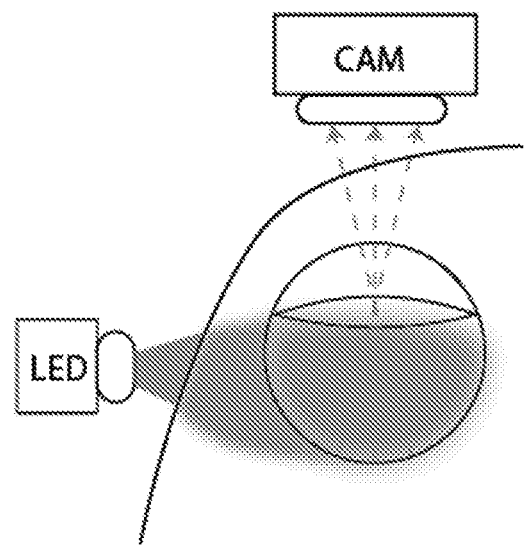
FIG. 13 schematically shows temporal illumination according to an aspect of the present invention: The light passes through the temporal tissues (skin) before reaching the sclera of the eye and the eye fundus.

In order to provide oblique back-illumination of the fundus, the following illumination can be used: transscleral (FIGS. 9A, 9B), transepidermal (FIGS. 10A, 10B), pupillary oblique illumination (FIGS. 11A, 11B), pupillary direct illumination (FIGS. 12A, 12B) or through the temple (FIG. 13).

With respect to dark-field collection, a collection method is described that collects only the light diffracted by sample and not from its background. Dark-field imaging of retinal layer is obtained by avoiding to illuminate the background of the imaged area thanks to high angle illumination or by filtering part of the background layer in a conjugate plane. This can be performed with flood illumination, scanning method and a mixture of the two, for example but not limited to flood illumination and scanning system for collection.

A scanning acquisition system can include, but is not limited to a confocal scanning acquisition, an optical coherence tomography acquisition, a shifted pupil scanning acquisition, a split detector acquisition, and a lock-in scanning acquisition. A detector can include but is not limited to a single pixel detector, a line camera and a 2D detector. A single pixel detector can include but is not limited to a photodiode, an avalanche photodiode, a photomultiplier tubes, a micro photomultipliers tube, a lock-in single pixel detector and a split detector composed of single pixel detectors. A two-dimensional detector can include, but is not limited to a lock-in multipixel detector, a CMOS camera, an sCMOS camera, a CCD camera, and a 2D split detector.

Next, different illumination methods and systems are described, with different configurations that serve as non-limiting and non-exclusive embodiments.

Configuration 1 (Transscleral)

Figure 9A:
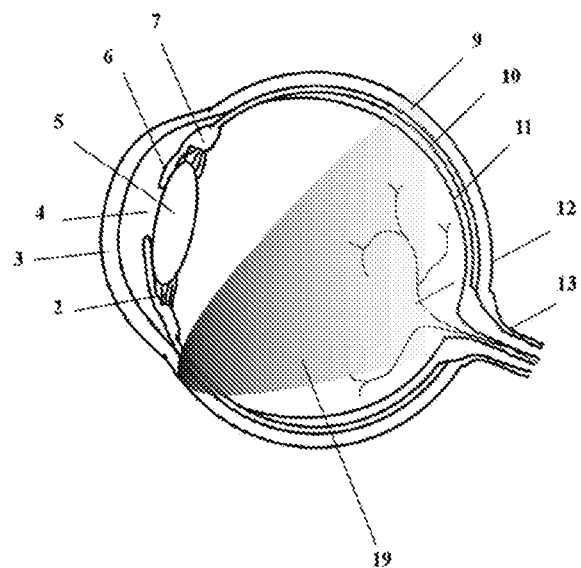
FIG. 9A schematically shows the transscleral illumination method according to an aspect of the present invention. Light passes through the sclera before illuminating the eye fundus.
Figure 9B:
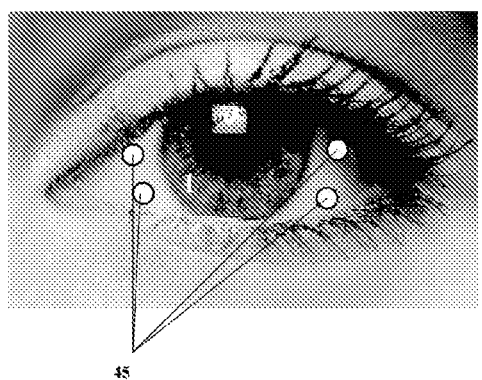
FIG. 9B schematically shows the proposed transscleral illumination method according to an aspect of the present invention: light is shined directly on the scleral tissue. Light can be delivered by direct contact of the source or the light waveguiding component, or in a non-contact manner with an optical beam (collimated or not). Some examples of a multiplicity of light position, areas are symbolized by discs. The scattering properties of the sclera produce a diffused beam that illuminates the fundus with a high angle. In case of physical contact with the sclera, local anesthesia can be used to make the measurement more comfortable to the patient.

Referring to FIGS. 9A and 9B, these figures represent the transscleral illumination method: light 16 is shined directly on the scleral tissue 9. Light can be delivered by direct contact of the source or the light waveguiding component, or in a non-contact manner with an optical beam (collimated, focused, diverging or with structured illumination). Some examples of light position are symbolized by discs 45. The scattering properties of sclera 9 and underneath layers 10, 11 produce a diffused beam 19 that illuminates the fundus with a high angle. In case of physical contact with the sclera, local anesthesia can be used to make the measurement more comfortable to the patient.

Structured illumination can include but is not limited to a sinusoidal phase pattern, a sinusoidal intensity pattern, a light pattern modulated in intensity with a micromirror array, a light pattern modulated in phase and/or with a spatial light modulator.

Waveguides and waveguiding components can include but are not limited to: single mode fibers, multimode fibers, capillary waveguides, lensed multimode fibers and photonics crystal fibers.

Configuration 2 (Transepidermal)

Figure 10A:
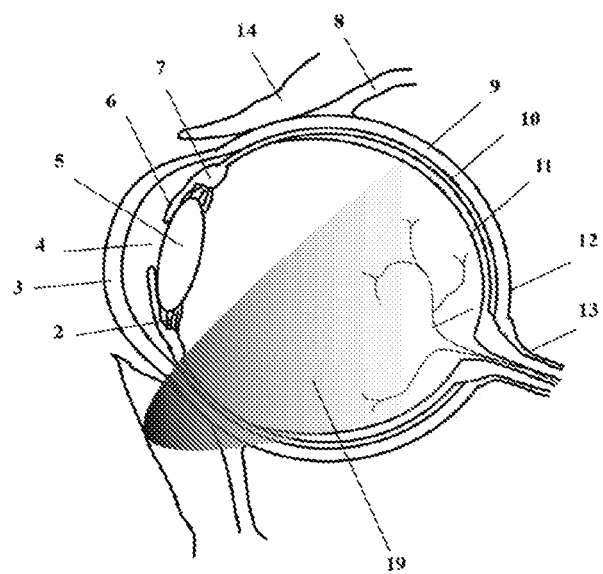
FIG. 10A schematically shows a trans-epidermal illumination method according to an aspect of the present invention. Light passes through the skin and the sclera before illuminating the eye fundus.
Figure 10B:
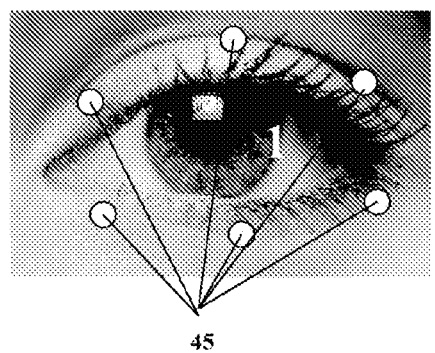
FIG. 10B schematically shows a trans-epidermal illumination method according to an aspect of the present invention. Light is shined on the eye lid and from there, scattered through different layers up to the inside of the eye. Light can be delivered by direct contact (of the source or a waveguiding component) or with an optical beam (collimated or not). Some examples of a multiplicity of light position, areas are symbolized by discs. Many point sources that are spatially separated provide different angles of illumination. Also contact with the skin can be more comfortable for a patient as it does not require anesthesia.

Referring to FIGS. 10A and 10B, these figures represent the transepidermal illumination method: light 16 is shined on the upper 14 and/or lower 15 eyelid and from there, scattered 19 through different layers up to the inside of the eye 1. Light can be delivered by direct contact (of the source or a waveguiding component) 27 or with an optical beam 16

(collimated or not). Some examples of light positions are symbolized by discs 45. Many point sources that are spatially separated provide different angles of illumination. Also contact with the skin can be more comfortable for a patient as it does not require anesthesia.

Configuration 3 (Transpupillary from the Side)

Figure 11A:
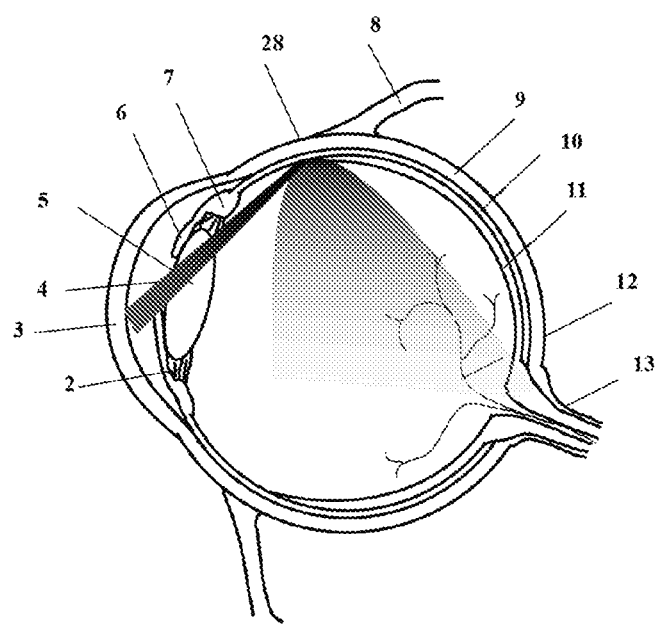
FIG. 11A schematically shows a pupillary illumination method according to an aspect of the present invention. Light is shined on the inside layers of the eye after passing through the pupil. The light is scattered on the inside of the eye and illuminating the eye fundus. Light can be delivered by direct contact (of the source or a waveguiding component) on the cornea or in a non-contact manner with an optical beam (collimated or not)
Figure 11B:
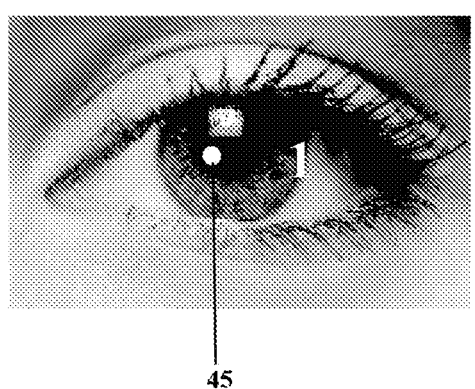
FIG. 11B schematically shows a pupillary illumination method with an example of point light entering in the pupil, according to an aspect of the present invention.

Referring to FIGS. 11A and 11B, these figures represent the pupillary illumination method: light 17 is shined on the inside layers of the eye after passing through the pupil 4 and the lens 5. The light is scattered on the inside of the eye after back reflection from the focal point 28 and illuminating the eye fundus. Light can be delivered by direct contact (of the source or a waveguiding component) on the cornea 3 or in a non-contact manner with an optical beam (collimated or not).

Configuration 4 (Transpupillary Direct Brightfield)

Another illumination method is based on direct illumination of the eye fundus. Once light reaches the eye fundus the backscattered light is modulated by the retina and then collected for imaging purposes. In this configuration light can shine either on the background of the imaged area (brightfield) or only on the side of it (darkfield).

Configuration 5 (Transpupillary Direct Darkfield)

Referring to FIGS. 12A and 12B, in these figures it is shown that light is sent through the pupil directly on the imaged retinal area. However, light is sent with such an angle that is not reaching the RPE on the back of the imaged retinal area. In this way the background appears dark. The light collected by this retinal area is not given by modulation of the background light, but to diffraction of the retinal features.

Configuration 6 (Mertz-Like)

Light is shined through the pupil and focused on the RPE without shining directly on the imaged retinal area or its background. Light scatters inside RPE and choroid, reaching the layer on the back of the imaged retinal area. From here light is backscattered and shined on the retina providing illumination.

Configuration 7 (Trans-Temporal)

Referring to FIG. 13, this figure shows the eye fundus can be illuminated also through transtemporal illumination. Light is shined on the patient's temple and from here it scatters into the eye.

Configuration 8 (Beam Shape)

Figure 14A:
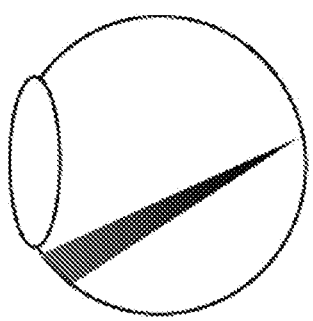
FIG. 14A schematically shows oblique illumination of the eye fundus with a focused beam according to an aspect of the present invention.
Figure 14B:
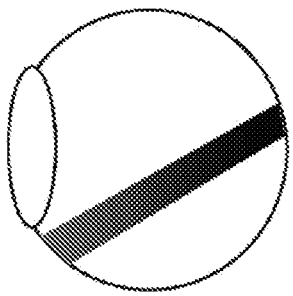
FIG. 14B schematically shows oblique illumination of the eye fundus with a collimated beam according to an aspect of the present invention.
Figure 14C:
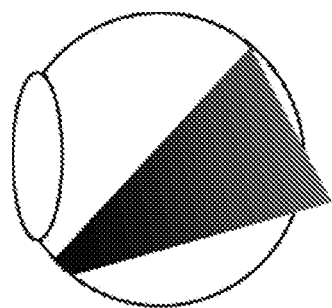
FIG. 14C schematically shows oblique illumination of the eye fundus with a diverging beam according to an aspect of the present invention.
Figure 15:
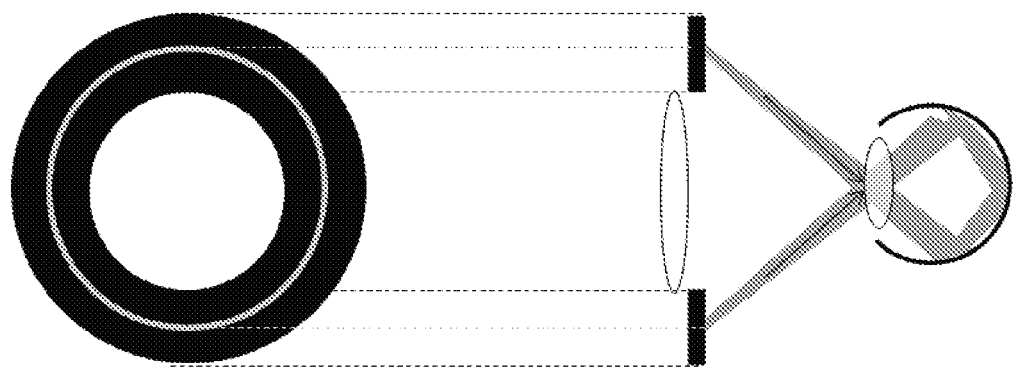
FIG. 15 schematically shows annular illumination using the side eyeball as scattering layer for proving high numerical aperture according to an aspect of the present invention.

Referring to FIGS. 14A, 14B, 14C, these figures show that, using Configuration 1 to 7, the beam shape can be modified thanks to, but not limited to, optical methods, wavelength choice, wavefront shaping.

Next, different exemplary illumination methods systems are discussed, as non-limiting and non-exclusive embodiments.

Configuration 1 (Contact Pcb)

Referring to FIGS. 23, 24, 25, 26, 27, 28A, a transepidermal illumination method is represented. Light 16 is shined on the upper 14 and lower 15 eyelid either simultaneously or sequentially or in any combination and from there, scattered 19 through different layers towards the inside of the eye 1. Light is delivered by direct contact of the light source 27 to the skin 15. A transparent or scattering media can be present between source and skin, to expand the illuminated area and decrease the power density on the skin. Illustrative examples of light source positions are symbolized by discs 45. Many point sources that are spatially separated provide different angles of illumination to the inside of the eye. Also contact with the skin can be more comfortable for a patient as it does not require anesthetic lubricant as opposed to the case of a light source in contact with the eye (sclera, cornea).

Figure 25:
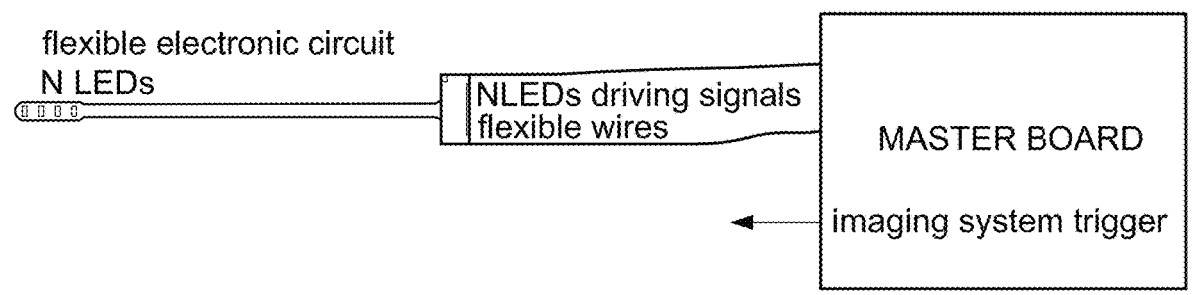
FIG. 25 schematically shows a simplified view of the printed circuit board (PCB) system with its electronic components, according to an aspect of the present invention.
Figure 26:
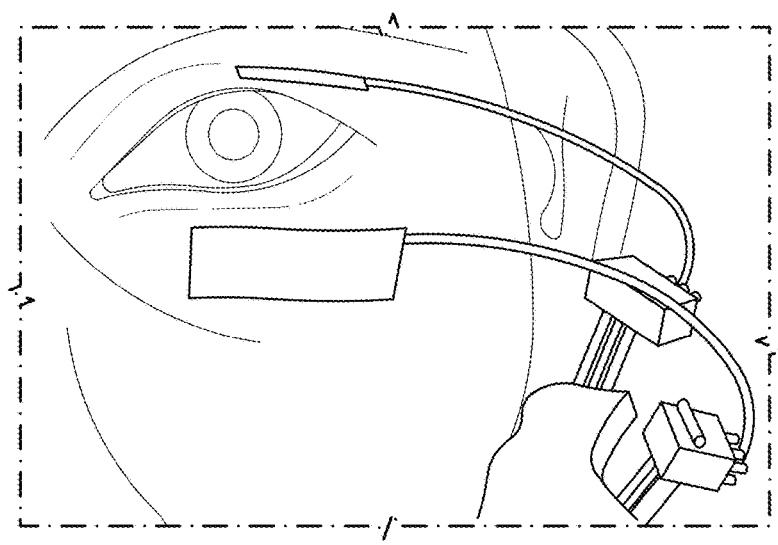
FIG. 26 shows a photograph of two prototypes placed on a subject's left eye. Four (4) light-emitting diodes (LED) can shine light from the top lid and four (4) other LEDs are shined from the bottom lid of the eye.
Figure 27:
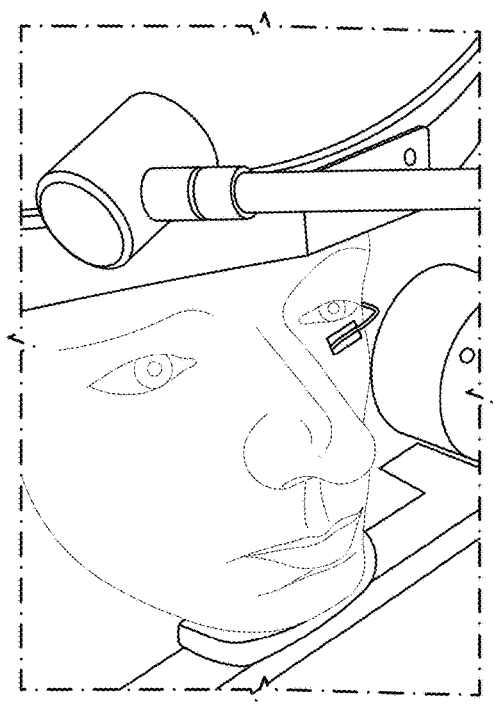
Figure 28A:
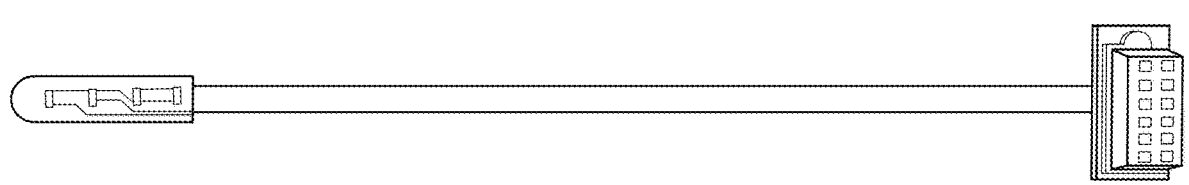
FIG. 28A shows a photograph of a designed prototype holding four (4) red surface-mount device (SMD) LEDs having a dimension smaller than 1 mm3. The illuminating device if a flexible PCB.

In the apparatus of FIGS. 25 and 28A the transscleral illumination system is connected to a master driver board. The board provides driving signals for all the LEDs connected to it, as well as the trigger signal for the imaging device in order to synchronize the illumination to the acquisition system. By turning on different LEDs a different illumination spectrum, both in terms of emitting wavelength and angular spectrum can be generated. By changing the driving current it is possible to change total intensity, shape of the power spectrum and spatial distribution of light.

Configuration 2 (Contact Pcb)

Figure 24:
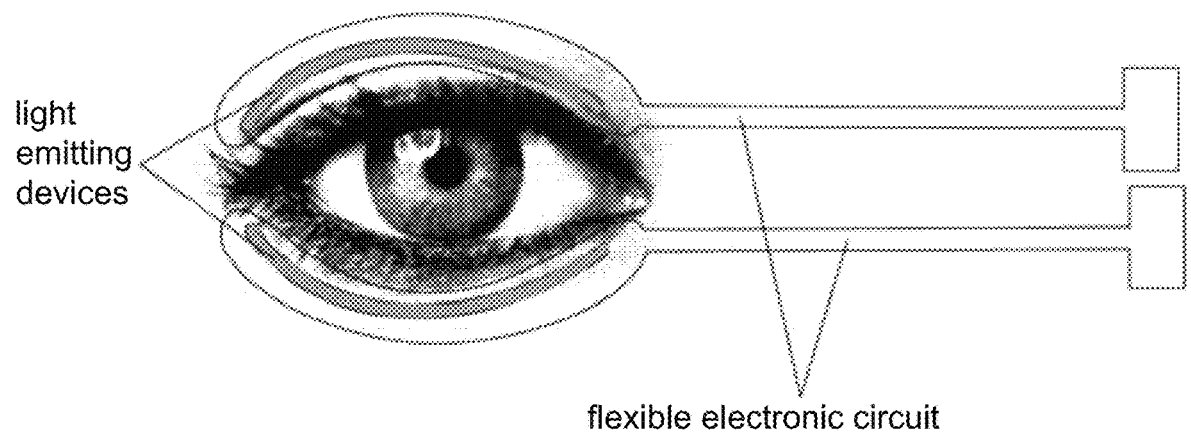
FIG. 24 schematically shows an illustration of a continuous light emitting device having the arc shape of the eye. The light emitting device is held by a flexible electronic circuit.

Referring to FIG. 24, a similar illumination principle to configuration 1 is shown, i.e. transepidermal illumination before passing through the sclera. The light emitting device and its flexible part has a continuous light source on top and bottom of the eye, following the arc shape of the eyelids. The continuous source is composed of pixels, each one of those can be switched ON or OFF independently.

Configuration 3 (Contact LED)

Figure 28B:
FIG. 28B shows a photograph of a prototype holding four (4) red LEDs having a diameter of 5 mm. The LED connectors are fixed to a threaded tube that can be screwed to the optical system.

Referring to FIG. 28B, a similar illumination principle to configuration 1 is shown, i.e. transepidermal illumination before passing through the sclera. The light emitting device is a LED, having an encapsulation of a transparent material (such as but not limited to epoxy and Polydimethylsiloxane) with a diameter of a few millimeters. The LEDs are placed in contact with the skin of the eyelids of the patient. The number of LEDs is not limited to 4.

Configuration 4 (Non Contact)

The illumination is provided in non-contact fashion, the beam illuminating the eye or the surrounding tissues can be focusing, collimated or diverging.

Configuration 5 (Wheel)

Figure 8:
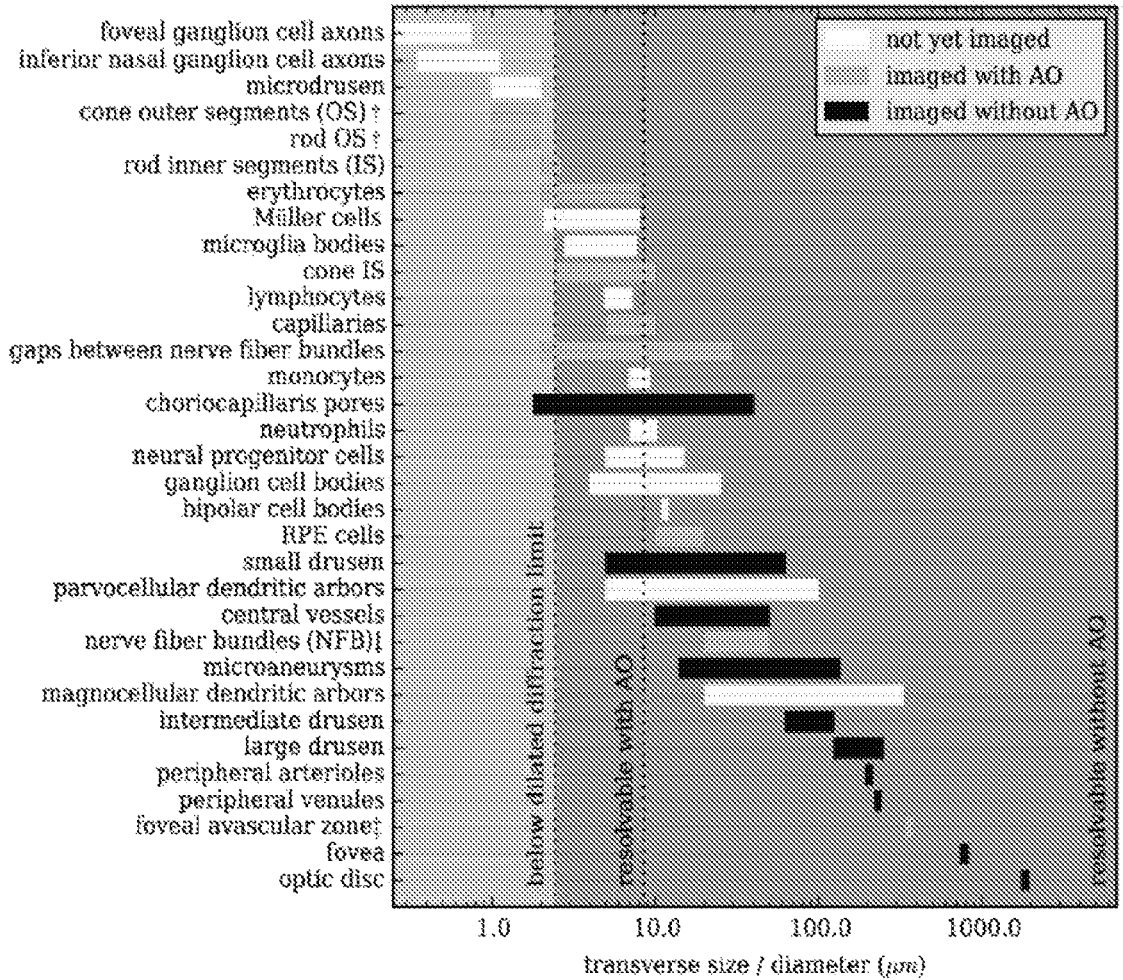
FIG. 8 shows a review based on state of the art OCT retinal imaging systems, table from Jonnal R. S., Kocaoglu O. P., Zawadzki R J., Liu Z., Miller D. T., Werner J. S., A Review of Adaptive Optics Optical Coherence Tomography: Technical Advances, Scientific Applications, and the Future. Invest Ophthalmol Vis Sci. 2016 Jul. 1; 57(9): October 51-68, showing the cells not being yet imaged in vivo, according to the background art.
Figure 19:
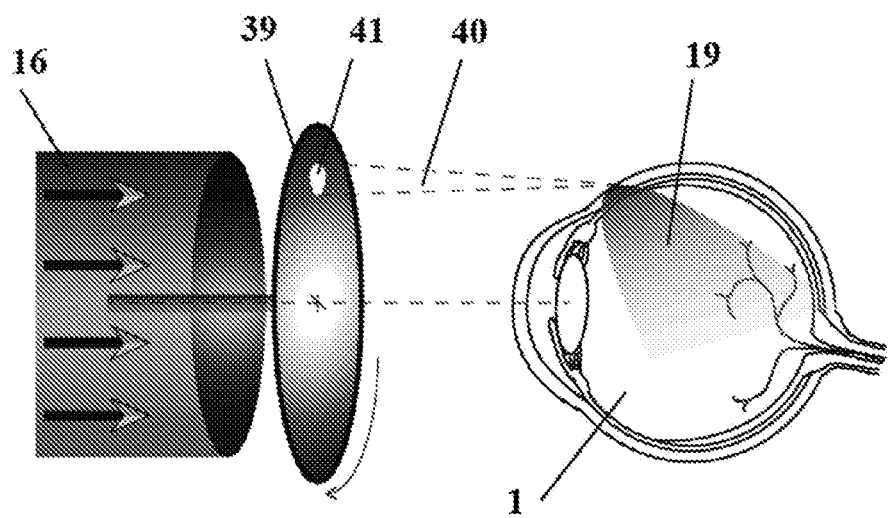
FIG. 19 schematically shows an apparatus for non-contact illumination according to an aspect of the present invention. A rotating wheel is pierced with a hole on its periphery. A light beam illuminates the whole surface of the wheel in such a way that the light passes only through the hole and illuminates only on point on the sclera. Alternatively, the illumination point can be on the skin.
Figure 21:
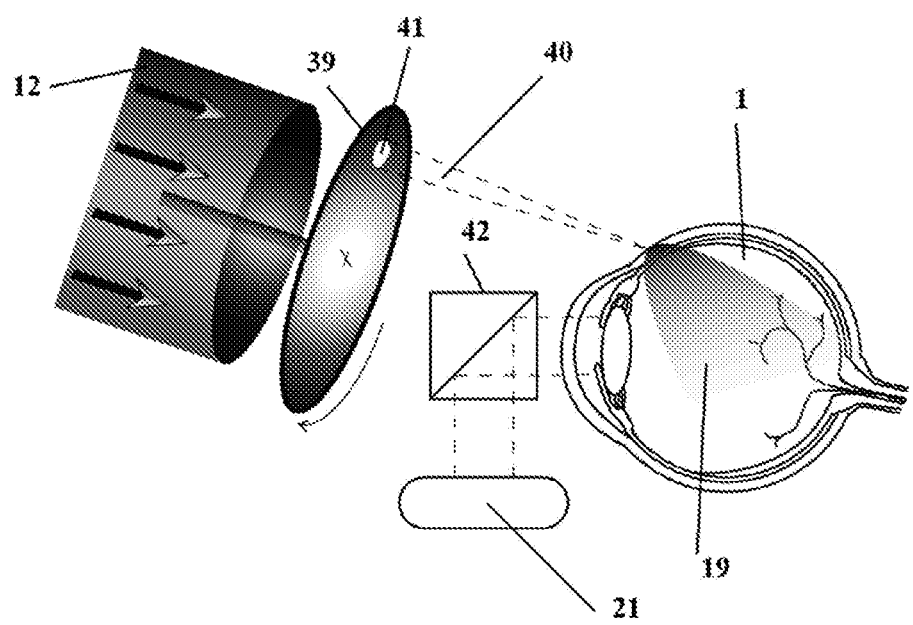
FIG. 21 schematically shows an apparatus for non-contact illumination, based on the example of the apparatus shown in FIG. 19 with the imaging system, according to an aspect of the present invention.
Figure 22:
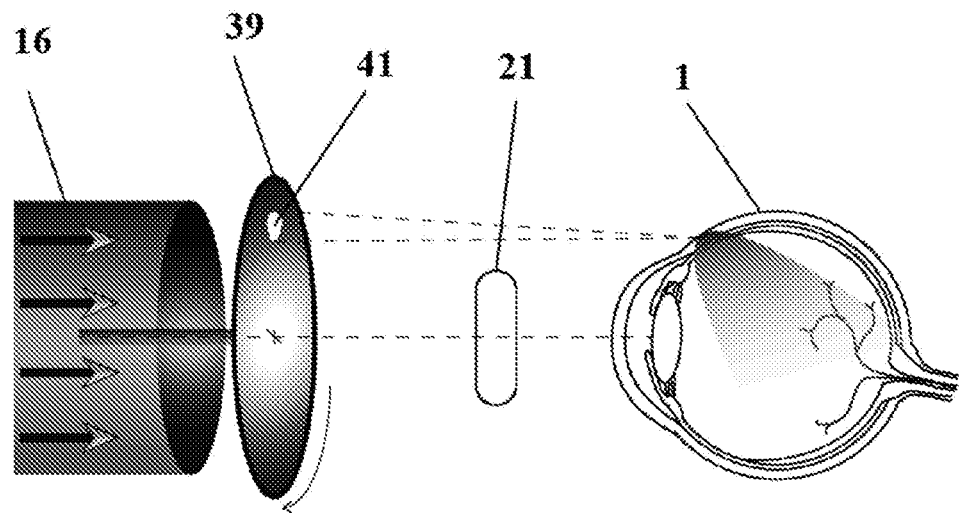
FIG. 22 schematically shows an apparatus for non-contact illumination, based on the example of the apparatus shown in FIG. 19 with the imaging system, according to an aspect of the present invention.

In the apparatus of FIGS. 19, 21 and 22, light directed to a scattering tissue is provided by, but is not limited to a light beam 16 and a rotating wheel 39 pierced with a small hole 41. A light beam illuminates the whole surface of the wheel, in such a way that light passes only through the hole 40 and illuminates only one point on the sclera 9. Alternatively, the illumination point can be on the skin 14, 15 surrounding the eye, or even on the lateral side of the eye, referring to FIGS. 4, 8 and 9.

Configuration 6 (Wheel and Fiber)

Figure 20:
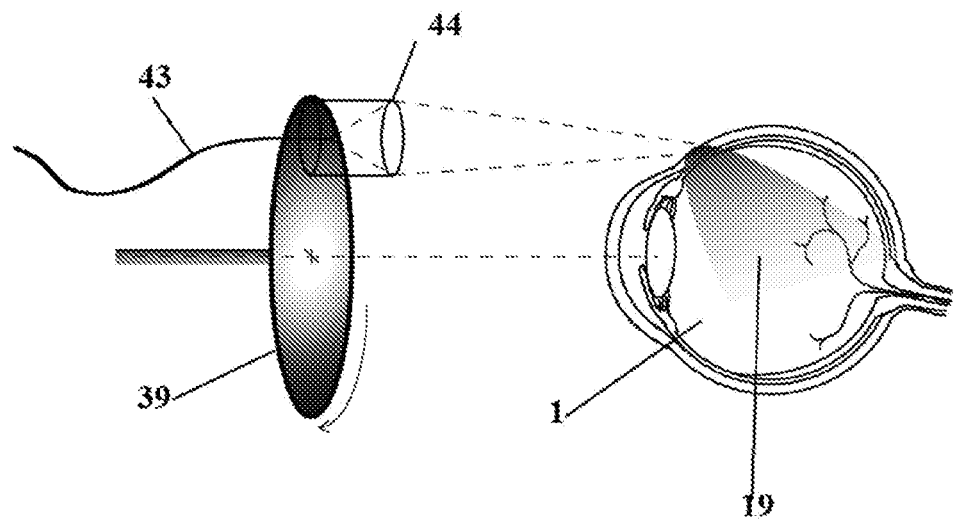
FIG. 20 schematically shows an apparatus for non-contact illumination according to an aspect of the present invention. A rotating wheel holds a fiber and a lens that focuses light on the sclera or on the skin.

In the apparatus of FIG. 20, light on scattering tissues is provided by a fiber 18 which can be, but is not limited to a single mode or multimode fiber. A rotating wheel 39 holds a fiber 18 and a lens 22 that focuses light on the sclera 9 or on the skin 14, 15. The fiber holder is designed in such a way that fiber can rotate freely, without introducing stress in the fiber. Furthermore, the disc holding the fibers is spun a limited amount of times, preventing the fiber to get coiled around the rotating arm. Another solution of preventing coiling consists of rotating the disc from the sides (and so removing any rotating arm).

Figure 16:
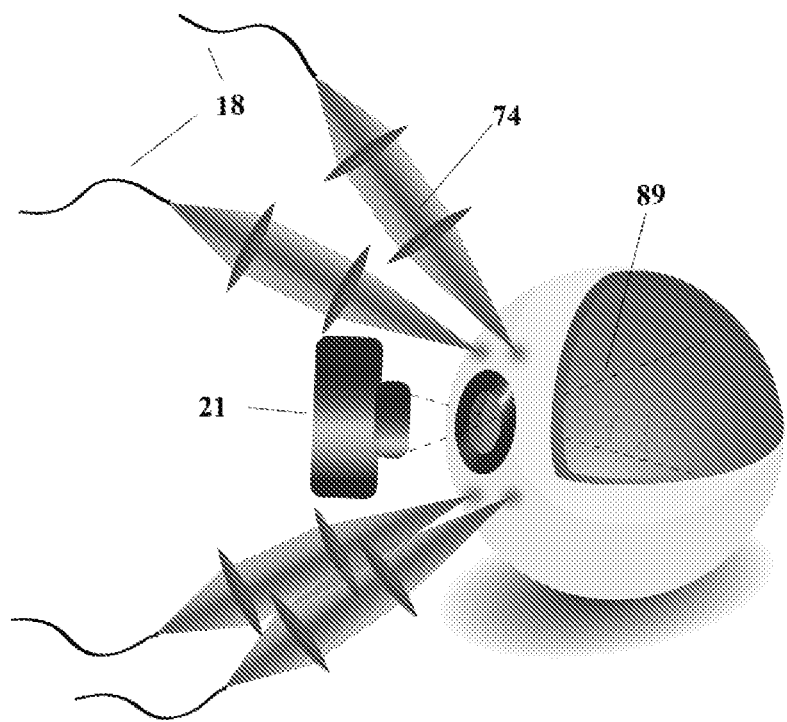
FIG. 16 schematically shows an exemplary apparatus for non-contact illumination according to an aspect of the present invention. Four (4) beams shining at four (4) different illumination points as a mean to illustrate the method, are represented.
Figure 18:
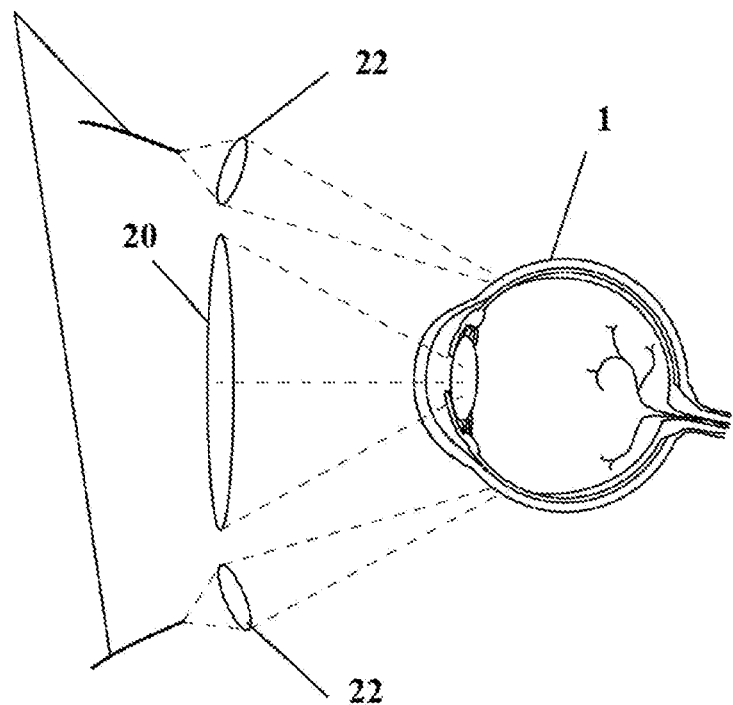
FIG. 18 schematically shows an apparatus for non-contact illumination, according to another aspect of the present invention, a top view of FIG. 17. Note that this figure differs from FIG. 2 in the number of illumination points (more than two), and the way of illumination. Here the beams are switched on sequentially (one or multiple at the same time), while in FIG. 2, the two points are shined simultaneously.

Another embodiment consists in a series of light sources arranged on a fixed structure shaped like but not limited to a circle (annulus). Alternatively, the light beams 74 can be separated, as shown in FIGS. 16 and 18. In these previous examples, the apparatus is configured to send the light in a non-contact manner, referring to FIGS. 10A to 14C.

Figure 23:
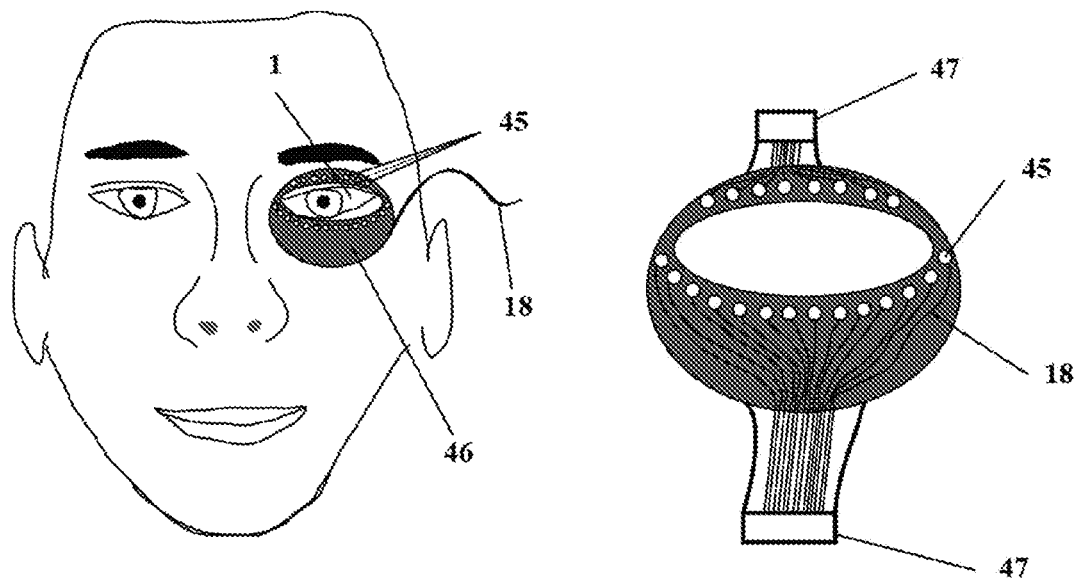
FIG. 23 schematically shows an apparatus for contact illumination according to an aspect of the present invention. A patch is put in contact with the patient's skin. The patch is connected to several fibers whose distal ends are the illumination points (area) on the patient's eyelids. The patch can be composed of a removable (consumable) protection part in contact to the skin (one per patient)

Configuration 7 (Patch):

In the apparatus of FIG. 23, light is delivered on the patient's skin, in contact with the skin thanks to a patch 46. The patch is connected to several fibers which brings several illumination points 45 on the patient's eyelids. Every illumination points require one optical fiber 18. The patch can be composed of a consumable protection part in contact to the skin. The patch is connected to the split light source thanks to optical connectors 47.

Figure 2:
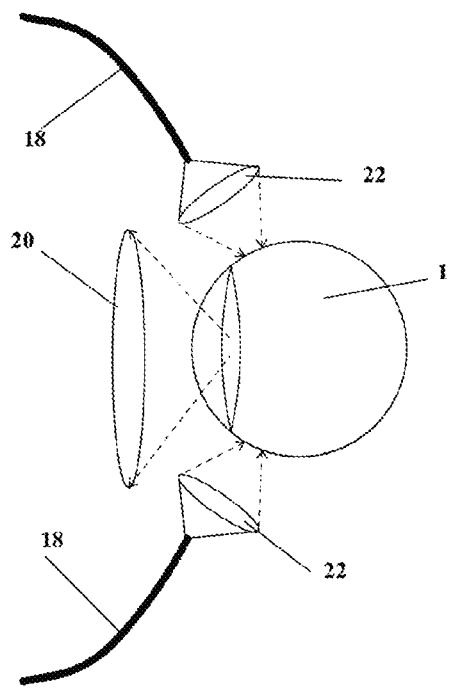
FIG. 2 shows a scheme of the working principle of the system presented in U.S. Pat. Pub No. 2007/0159600 according to the background art. The method uses one illumination point, or two illumination points where the two sources provide illumination simultaneously.
Figure 17:
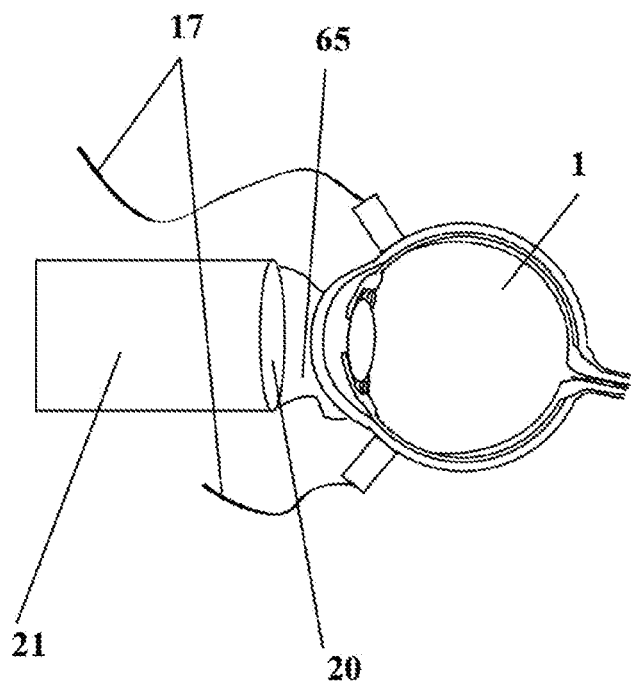
FIG. 17 schematically shows a top view of an apparatus for contact illumination, according to another aspect of the present invention. At least one light beam is in contact with the sclera. The light beam can be brought via a light waveguide such as but not limited to a multimode fiber. In addition, the imaging lens that images the fundus through the eye lens is also in contact with the sclera via an index matching gel placed between the cornea and the imaging lens. Note that this figure differs from the apparatus shown in FIG. 2 in the number of illumination points (more than two), and the way of illumination. Here the beams are switched on sequentially (one or multiple at the same time), while in FIG. 2, the two points are shined simultaneously.

Configuration 8 (Contact Sclera):

In the apparatus of FIG. 17, light is delivered on the patient's sclera 9, in contact. The light comes out from multiple optical fibers 18 or optical waveguides. In addition, the objective of the imaging system 21 is almost in contact with the cornea 3, an index matching, bio-compatible gel 65 being in between the two. Note that the principle showing in FIG. 17 differs from the FIG. 2 in the number of illumination points (more than two), and the way of illumination. Here the beams are switched on sequentially, while in FIG. 2, the two points are shined simultaneously.

Figure 54:
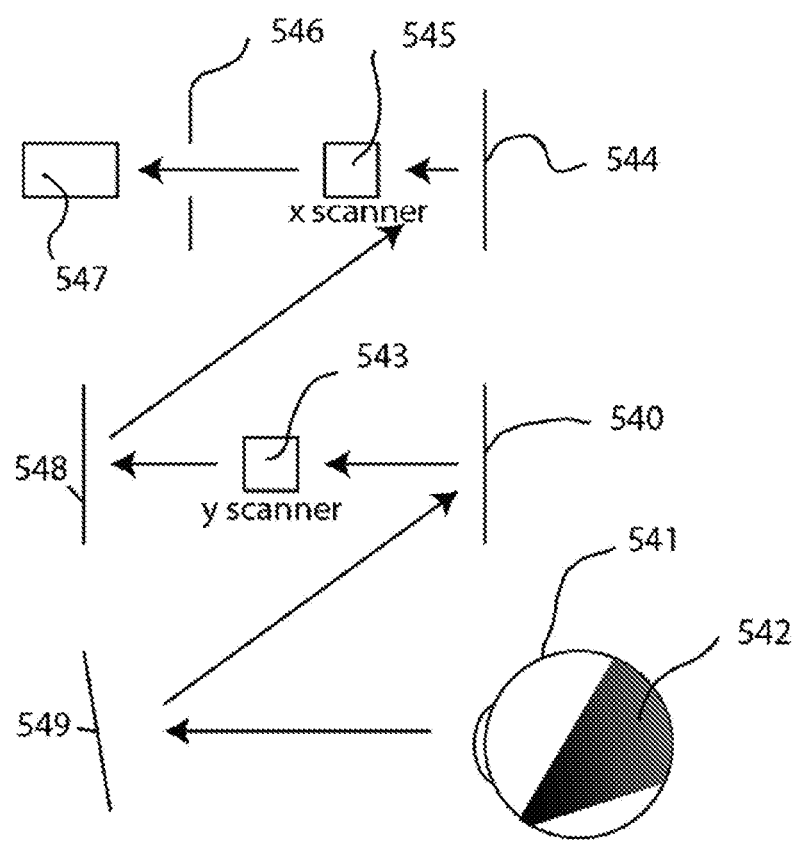
FIG. 54 shows a schematic representation of an operational scheme or method for a scanning system using transscleral illumination, according to an aspect of the present invention.

FIG. 54 shows an exemplary schematic view of a scanning system for inspecting eye 541, according to an aspect of the present invention. The use of a scanning system for signal collection allows for a better depth selectivity of the imaging layer of the sample. It can be used for collecting both phase/absorption or darkfield information. The system uses a scanning element, such as but not limited to a two-axis scanning mirror 543 and 545 for scanning the collection beam along the imaged area on eye 541. Other mirrors 540, 544, 548 and 549 are used to reflect the light towards a detector. A diaphragm or a pinhole 546 is then placed in a plane conjugate to the imaging plane. In this way depth selection is improved. Compared to a standard SLO system, only the detection arm is needed because the illumination 542 is provided through the sclera, and not through the pupil. The use of a scanning system can be also combined with hardware adaptive optics. The signal is collected by a single pixel detector 547 such as but not limited to photodiode, avalanche photodiode, photomultiplier tube (PMT), micro-PMT which can be used for a standard acquisition or in a lock-in mode.

Figure 55:
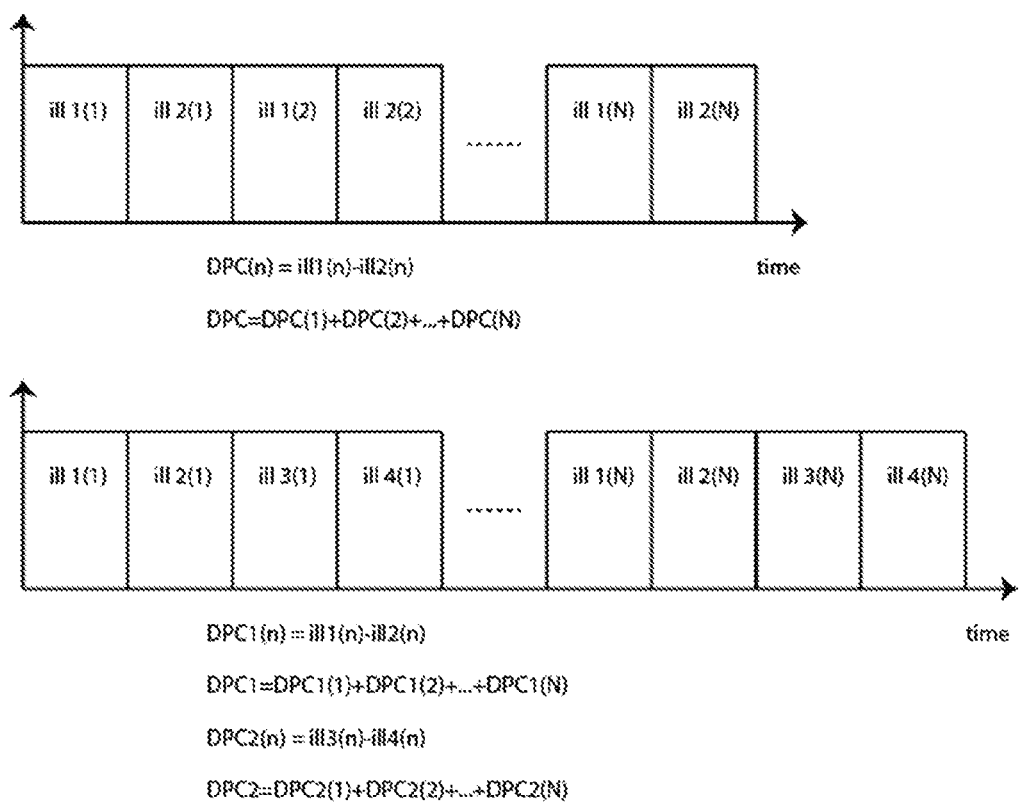
FIG. 55 depicts signals in the form of chronograms illustrating a lock-in acquisition, according to an aspect of the present invention.

Referring to FIG. 55, a lock-in acquisition can be efficiently integrated to the system. The lock-in acquisition can be performed using a lock-in camera, for instance in flood illumination, or a single detector, for instance in a scanning system. The output of the camera/detector is then the DPC image. In addition, several DPC signals can be integrated to have an output that is an average value of the DPC signal. It allows to increase the SNR. Finally, removing the background at an early stage of the readout chain provide a more efficient use of the digital resources.

Figure 29:
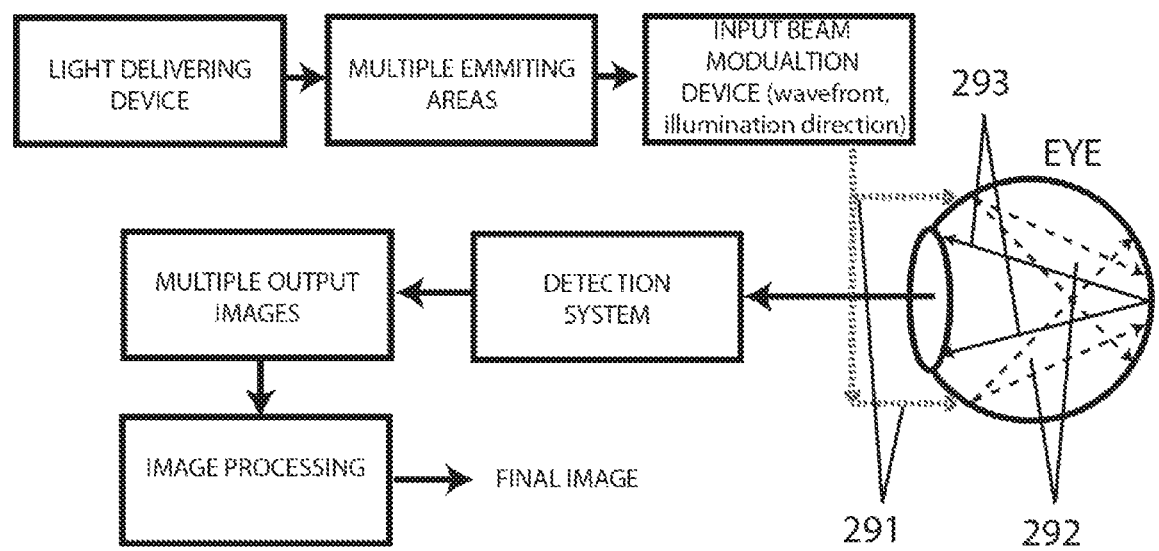
FIG. 29 is a simplified representation of a schematic of the device, according to an aspect of the present invention. The light beam is first reshaped by the modulating device and then is sent to the retina with a high numerical aperture illumination method. The backscattered light is collected from the pupil and measured by a detector. Beam 1: forward scattered light. Beam 2: collected backscattered light.
Figure 30:
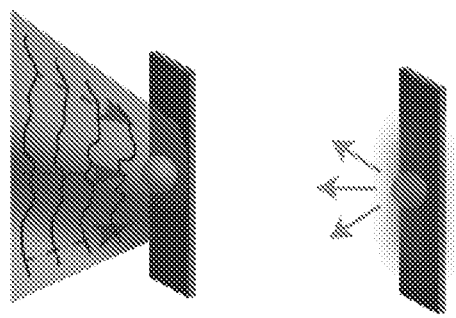
FIG. 30 shows a representation of the concept validation for focusing using dark background and a reflective bead. A generic wavefront is shined on the surface. Since only the bead can reflect light only a small amount of power is coming back.
Figure 31:
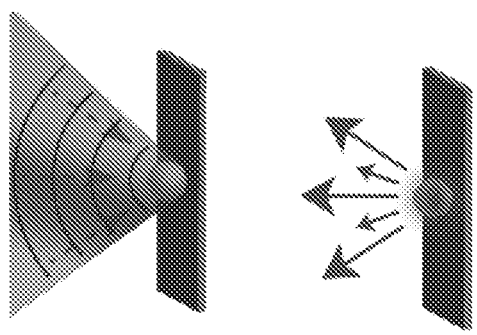
FIG. 31 shows a representation of the concept validation for focusing using dark background and a reflective bead. An optimized wavefront is shined on the surface. Light is focused on the bead reflecting back all the scattered light.

Wavefront shaping is further explained with respect to FIGS. 29, 30, and 31. The different illumination schemes provide, at the retinal surface a speckle pattern with a speckle grain size smaller than the photoreceptors' diameter, which are a few micrometers (D. Mustafi, A. and H. Engel, Krzysztof Palczewski "Structure of cone photoreceptors," Progress in Retinal and Eye Research, Vol. 28, No. 4, pp. 289-302, 2009). After the high resolution speckle pattern is shined on the fundus it is possible to reconstruct a high resolution image of the fundus in several embodiments.

A first embodiment includes the viewing (i.e. collecting the digital image) of the speckle pattern through the pupil of the eye (and so with a much lower resolution). Due to the scattering media's memory effect, it is possible to shift the speckle pattern and collect a picture for every shift. The resulting collection of images is then used in a phase retrieval algorithm to reconstruct an image of the fundus with the same resolution of the original high resolution projected speckle pattern. Another embodiment is to place markers on the surface of the eye, such as embedded within a contact lens or by displaying non-contact markers or any high resolution eye tracker, for the purpose of obtaining feedback to always illuminate the same area to provide a constant speckle pattern.

Another embodiment for image reconstruction is based on scanning a single focus spot. Due to wavefront shaping, it is possible to transform the speckle pattern into a single spot (of the same size as the original speckle). Similarly, in this method, the memory effect is used to scan the spot. By collecting the reflected intensity at each point, it is possible to reconstruct the intensity profile of the entire fundus image. The main difficulty of this embodiment lies in the focusing part, since the limited resolution caused by the pupil does not allow for the measurement of the transmission matrix. An alternative is the use of an iterative process, such as, but not limited to, a genetic algorithm (GA). (D. Conkey, A. Brown, A. Caravaca-Aguirre, and R. Piestun, "Genetic algorithm optimization for focusing through turbid media in noisy environments," Opt. Express, vol. 20, pp. 4840-4849, 2012). GA can provide focusing by maximizing a parameter that measures how close is the pattern to the ideal case (perfect focusing). This class of algorithm is the most efficient for the targeted application because of its fast convergence time, i.e. only about 1000 iterations are necessary for focusing light with an acceptable contrast (I. M. Vellekoop, "Feedback-based wavefront shaping," Opt. Express 23, 12189-12206 (2015)).

In the case of the eye fundus, the unique properties of this tissue can be used to provide a parameter for focusing. Cone photoreceptors (1-1.25 urn diameter (D. Mustafi, A. and H. Engel, Krzysztof Palczewski "Structure of cone photoreceptors," Progress in Retinal and Eye Research, Vol. 28, No. 4, pp. 289-302, 2009)) appear to be much brighter than the background because of their waveguiding properties (B. Vohnsen, "Photoreceptor waveguides and effective retinal image quality," J. Opt. Soc. Am. A 24, 597-607 (2007)-B. Vohnsen, I. Iglesias, and P. Artal, "Guided light and diffraction model of human-eye photoreceptors," J. Opt. Soc. Am. A 22, 2318-2328 (2005)), and their sparse distribution can be used for beating the resolution limit. It is straightforward to see that the maximization of the total reflectance coincides with the focusing of the light on the brightest photoreceptor. Another parameter that can be maximized is the total intensity in the area containing just one photoreceptor divided by the background intensity. When two or more points contribute to the generation of a PSF its ratio maximum/energy is smaller than the ideal case.

Figure 53:
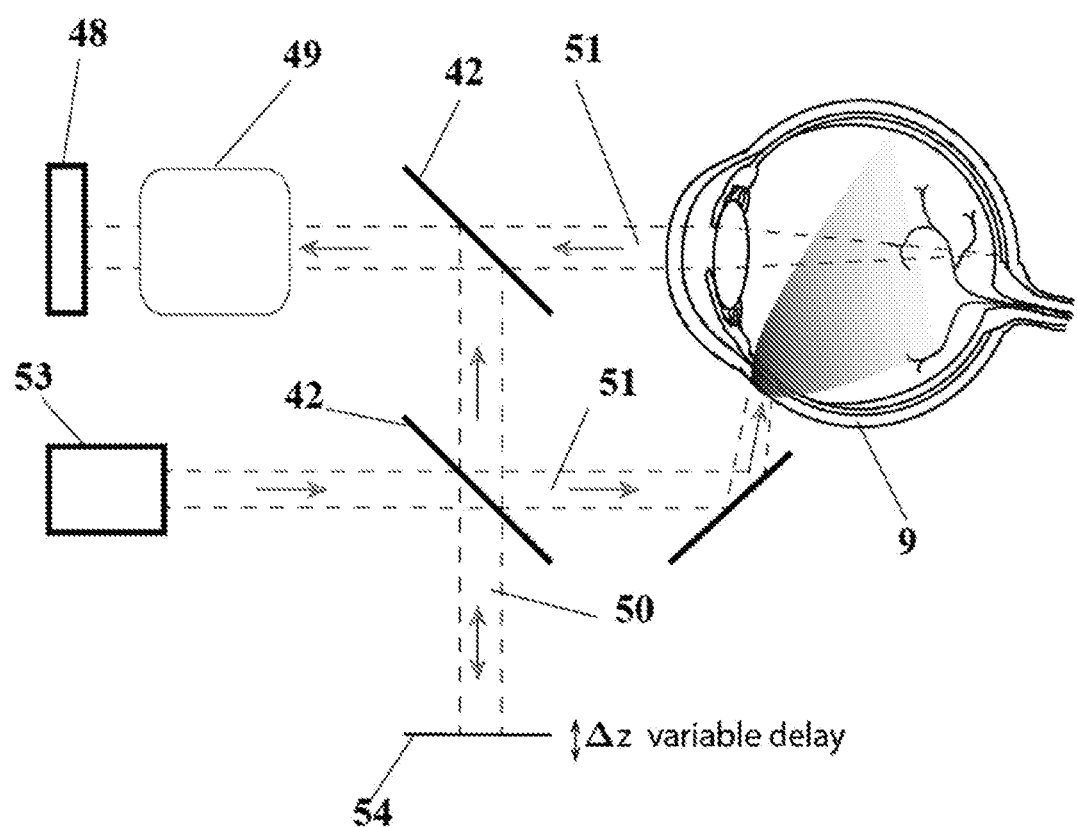
FIG. 53 shows a schematic representation of an optical system for an interferometric measurement with scattered light, according to an aspect of the present invention. A broadband light source (e.g. Superluminescent light emitting diode: SLD) is split into a reference and an object arm. The reference illuminates a mirror that can translate to scan the sample in depth. The object arm illuminates the eye with the methods described in FIGS. 4 to 26. After illuminating the fundus, the back-scattered light is collected by the pupil and interferes with the reference beam. Alternatively, a Fourier domain method can be implemented (not shown in the picture) by decomposing the spectral content of the scattered beam to retrieve depth in the retina.

Regarding interference imaging, FIG. 53 shows the optical principle scheme for optical coherence tomography measurement with scattered light. A broadband light source 53 (e.g. SLD) is split into a reference 50 and an object 51 arm. The reference 50 illuminates a mirror 54 that can translate to scan the sample in depth after interfering. The object arm illuminates the eye 1 through the skin 8 and/or the sclera 9, the choroid 10 and the retina 11. After illuminating the fundus, back-scattered light is collected by the pupil 4 and interferes with the reference beam. After recombining the two beams thanks to a beam splitter 42, the interfering beam passes through an imaging optics blocks 49 and is recorded by a detector 48.

Elements of the system can combined with other imaging modalities, for example but not limited to OCT, fluorescence imaging, magnetic resonance imaging (MRI), in a single platform to obtain and merge medical information helping for the diagnostic, to establish a multimodal retinal imaging platform. Especially the use of a scanning system for image acquisition makes the system more compatible with scanning laser ophthalmoscope and OCT technology.

Phase imaging of the retina with aspects of the present invention can be performed with infrared light. The human eye is not sensitive to infrared light. As a consequence, for the living retinal, some retinal function can be imaged by stimulating the retina with visible wavelength, for example through the pupil or the the sclera, to perform functional retina imaging. For instance, the response of the photoreceptors to different wavelength can be studied. The Functional analysis method, as used herein, can include but is not limited to a deep learning algorithm.

An ophthalmic imaging system can include, but is not limited to an optical coherence tomography system, an eye-fundus imaging system, a slit illumination imaging system, a fluorescing angiography imaging system, an indocyanine green angiography imaging system, a fundus autofluorescence imaging system, a corneal topography imaging system, a endothelial cell-layer photography imaging system, a specular microscopy system to provide multimodal imaging of the eye tissues.

The same imaging method can be applied for imaging the anterior part of the eye. The anterior eye tissue can include, but is not limited to the eye lens, the endothelium, and the cornea. Light scattered from the eye fundus or from the pupil is transmitted through the these layers and modulated in intensity and phase. The use of an imaging system whose focal plane is not the retina, but rather the front layers of the eye (e.g. the corneal endothelium) would allow recording of images containing phase and absorption information. In the same way, by recording two or more of these images using different illumination it is possible to reconstruct the absorption and phase profile.

Figure 38:
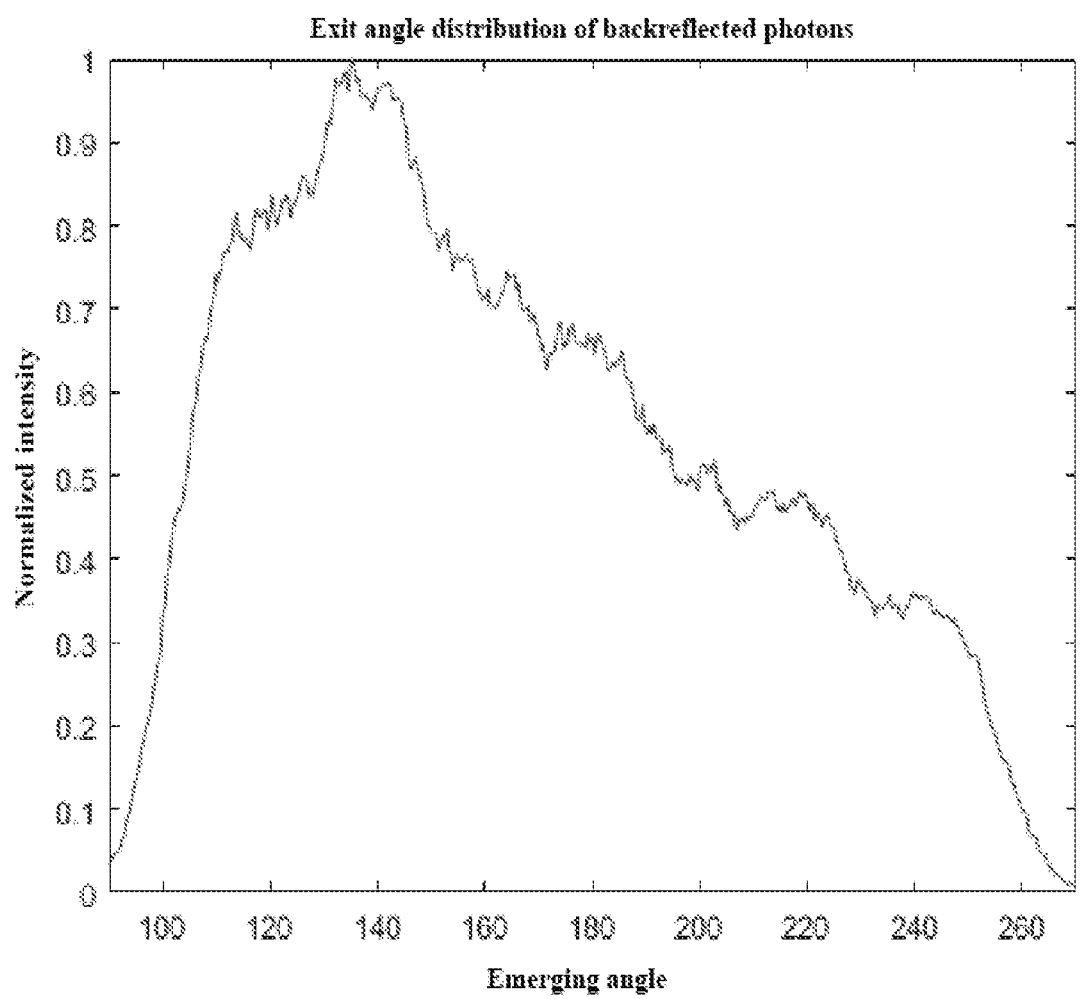
FIG. 38 is a graph representing the two-dimensional (2D) Monte Carlo simulation of angular distribution of the back-scattered light. The illumination beam is considered to impinge with an angle of 45°. The chosen scattering parameters are for choroidal tissue.
Figure 39:
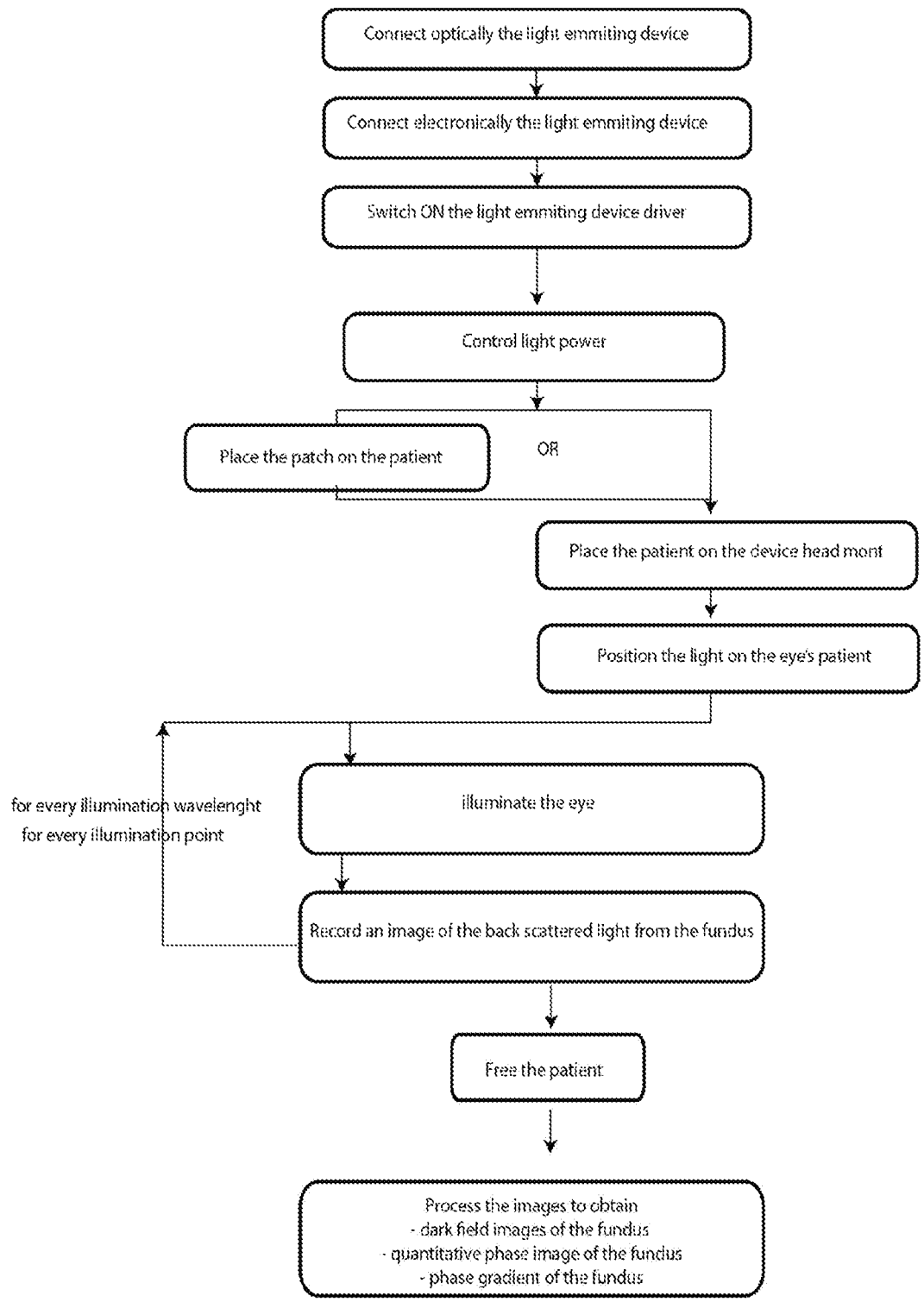
FIG. 39 shows a schematic representation of a flow chart for performing a measurement, according to an aspect of the present invention. The optical system is positioned on the patient by following the embodiments detailed in FIG. 9A to FIG. 28. After this step, each point is illuminated with one or more wavelength covering a spectrum approximately between 400 nm to 1200 nm and an image of the fundus is acquired through the eye lens. Each image is acquired sequentially. The patient's pupil maybe dilated but not limited to this case. In the case of dark field images (minimum 1 illumination point) the image captured is directly the dark field image. If the chosen method is phase imaging (minimum 2 illumination points) the acquired images need first to be processed to obtain a qualitative or quantitative phase image. When all the pictures have been acquired, the images can be post-processed.

Next, a general method describing a protocol for the imaging of the eye is described, with respect to FIG. 38. The optical system is positioned on the patient by following the embodiments in FIGS. 9A to 29. Next, the imaging system is aligned with the eye of the patient. After this step, each point (one at the time or multiple together) is illuminated with one or more wavelength selected in a spectrum approximately between 400 nm to 1200 nm and an image of the fundus is acquired through the eye lens. Each image is acquired sequentially. The patient's pupil may or may not be dilated. In the case of dark field images (minimum 1 illumination point) the image captured is directly the dark field image. If the chosen method is phase imaging (minimum 2 illumination points) the acquired images need first to be processed to obtain a qualitative or quantitative phase image. When all the pictures have been acquired, the images are post-processed.

A series of experimental tests have been performed that have shown operability, proof of principle, and substantially improved results over the background art.

Figure 46:
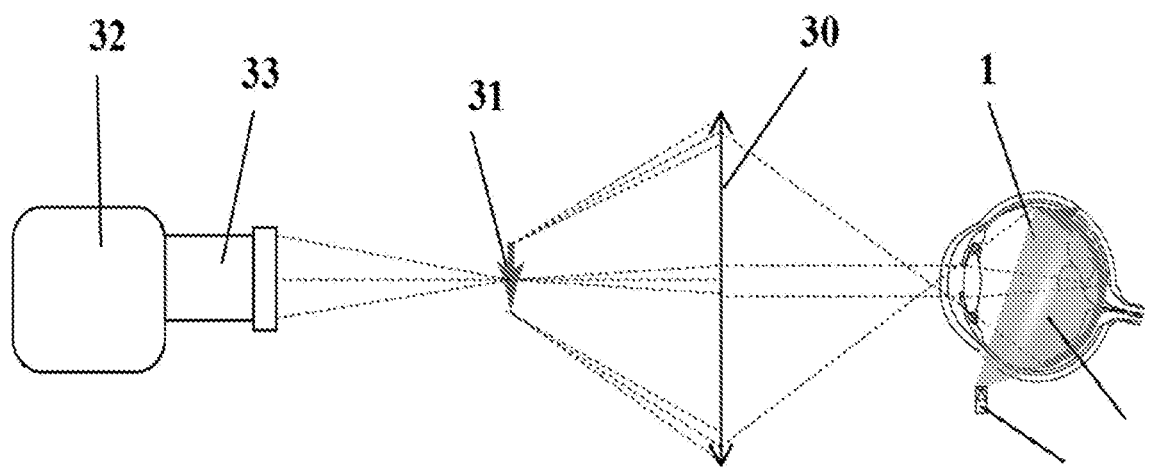
FIG. 46 shows a schematic representation of an optical system of the indirect ophthalmoscope used for the proof of concept measurements.
Figure 50:
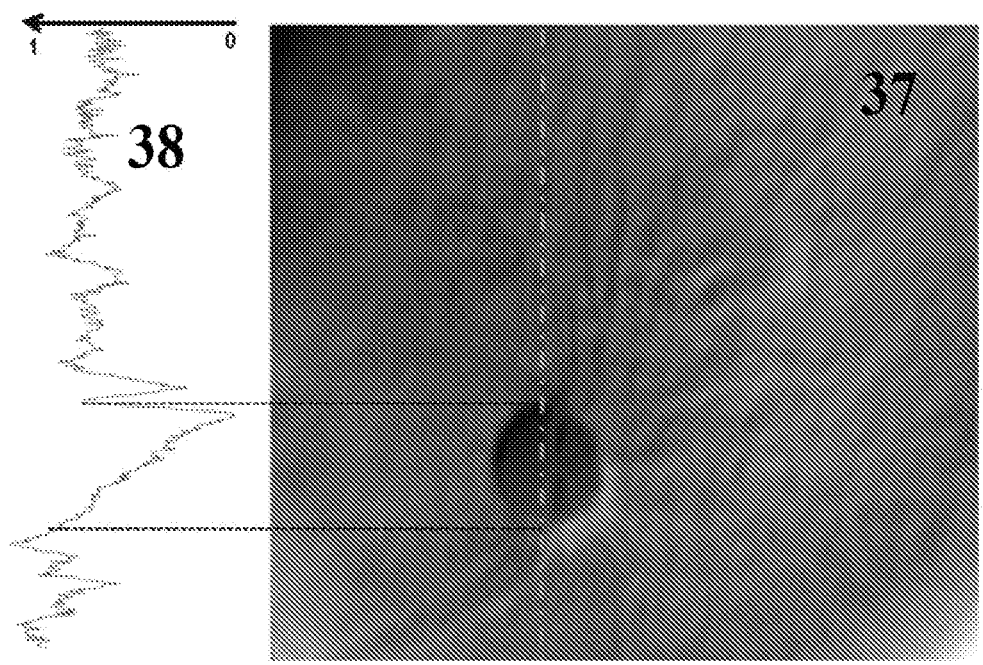
FIG. 50 shows a phase gradient image obtained with the method according to an aspect of the present invention, with corresponding cross-section showing gradients for the vessels, and the optic disc.

With respect to measurements related to in vivo phase imaging, for proof of principle demonstration, an indirect ophthalmoscope has been built, as shown in FIG. 46. The aspherical lens 30 allows a field of view in the fundus of about 60°. The camera objective 33 focuses at the image plane of the lens 30 and the camera 32 records the inverted image 31 of the eye's fundus. FIGS. 49, 50, 51 show two dark field images 35, 36 for two individuals and their corresponding phase gradient images 37 obtained by subtracting the two dark field images, using the relation of Equation (1). Illuminating wavelength was 643 nm. The left side of FIG. 49 shows a picture taken with transepidermal from bottom center point of illumination, the center shows a picture taken with transepidermal from bottom left point of illumination, and the right side shows the difference of the two showing the phase contrast. FIG. 18 shows the phase gradient image 37 with a line profile 38 showing gradient of the optic disc for example. Next, in FIG. 51, the left side shows a picture taken with transepidermal from bottom right point of illumination, the center shows a picture taken with transepidermal from bottom left point of illumination, and the right side shows a difference of the two showing the phase contrast.

Figure 47:
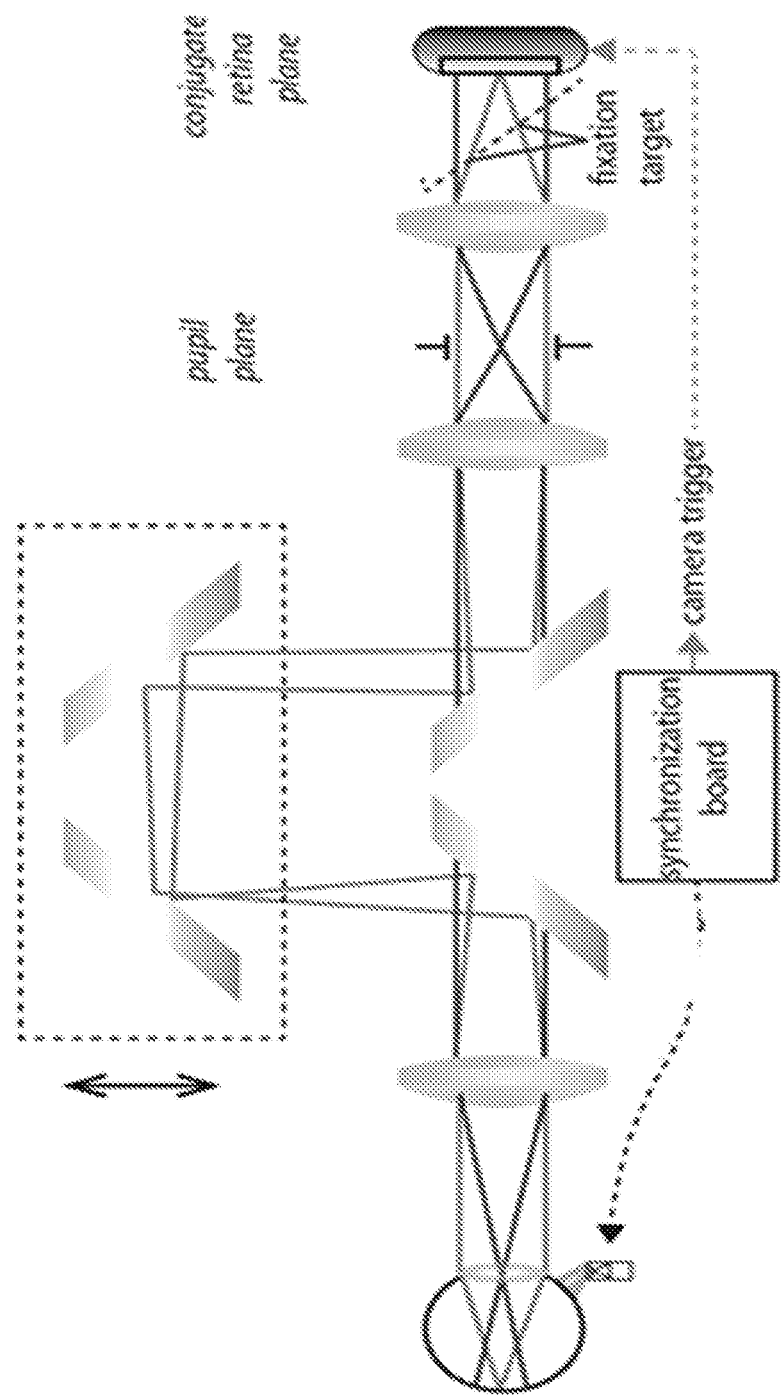
FIG. 47 shows a schematic representation of a system for in-vivo imaging, according to an aspect of the present invention. The LED used for transscleral illumination is synchronized with the acquisition of the camera. The pupil plane is conjugated to the plane of the diaphragm D. In this way light scattered around the eye is filtered from the final picture. The camera plane is conjugated with a plane in the retina, whose depth can be adjusted thanks to the badal system.
Figure 52:
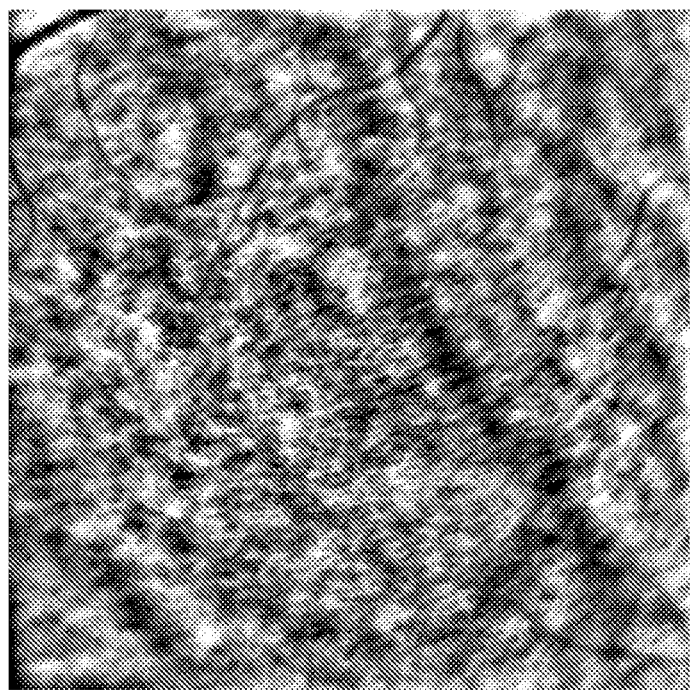
FIG. 52 shows an example of a darkfield trans-epidermal image acquired with the system of FIG. 47.

Referring to FIG. 47, in a second step another ophthalmoscope has been built in order to obtain a smaller field of view. It includes a stage for adjusting the focus, a fixation target for the patient and two telescopes formed by the eye lens, including the first lens, the second lens, and the third lens from left to right). In addition, a diaphragm is placed at the pupil plane to filter the beam. Finally, a high sensitivity camera record the retinal image. FIG. 52 shows an example of a 2×2 mm2 field of view of a retina with trans-epidermal LED (peak wavelength at 870 nm) illumination.

Referring to FIG. 48, in a third step a system has been designed to correct the aberrations using a wavefront sensor and a deformable mirror in closed loop using an aberration correction method.

An aberration correction method, as used herein, can include but is not limited to a deformable mirror, a spatial light modulator, a Badal system, a tunable lens, a series of cylindrical lenses, a Waller method, a modified Waller method, and a blind deconvolution algorithm.

Figure 42:
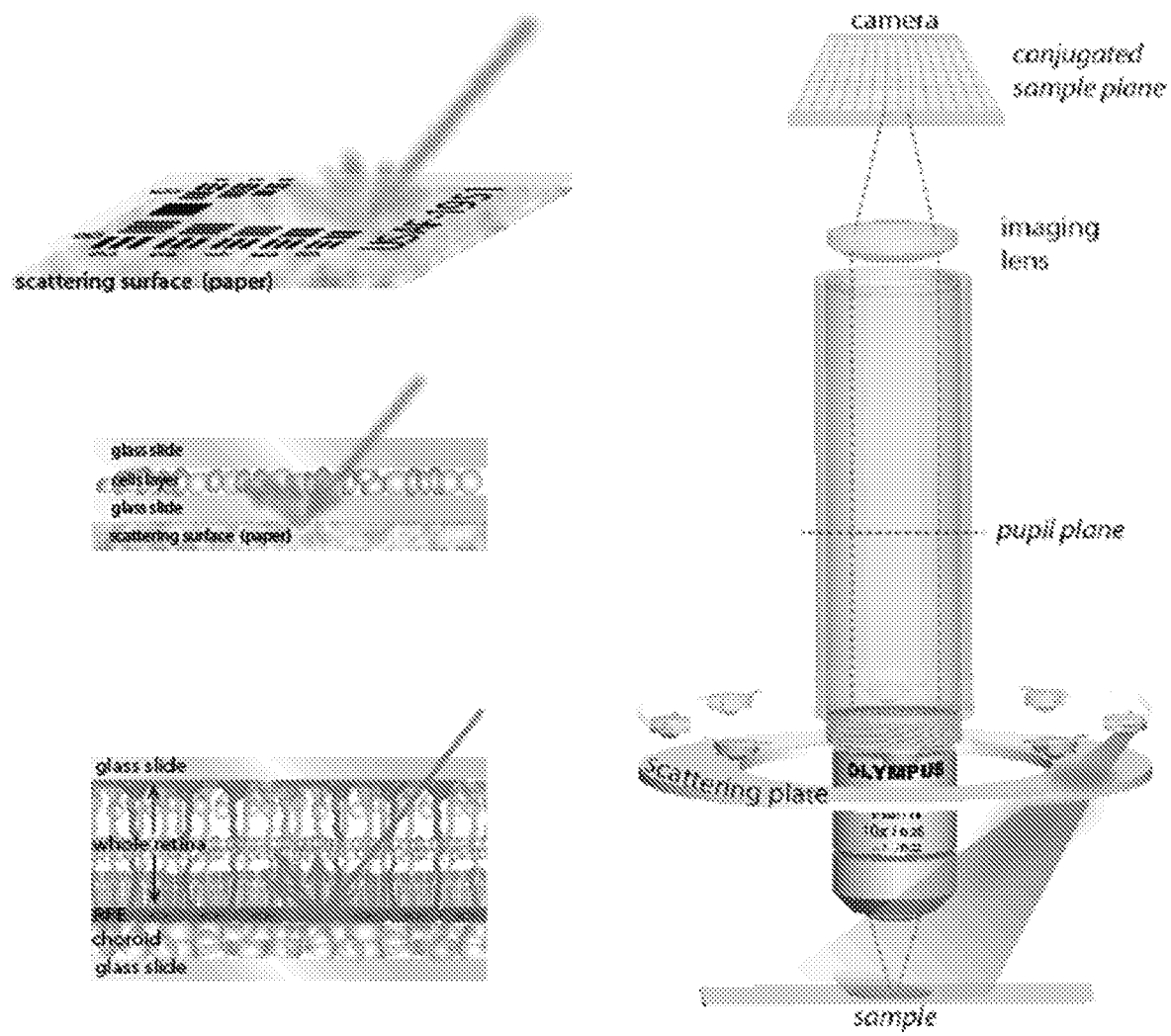
FIG. 42 shows a schematic view of a system or device used to perform ex-vivo measurements, according to an aspect of the present invention. Samples used for validation and proof of concept of phase imaging.
Figure 43A:
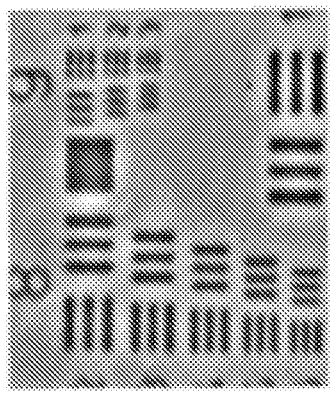
FIGS. 43A, 43B, and 43C depict measurements of the samples illustrated in FIG. 42. Comparison with digital holography providing quantitative phase measurement and confocal microscopy providing intensity measurement.
Figure 43A:
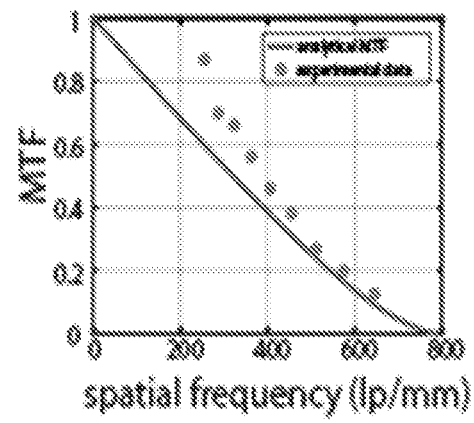
Figure 43B:
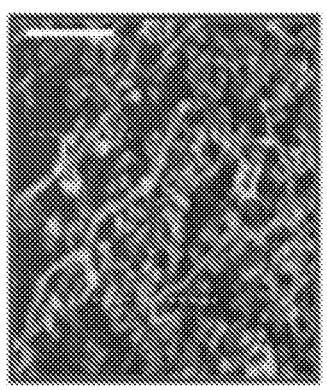
Figure 43B:
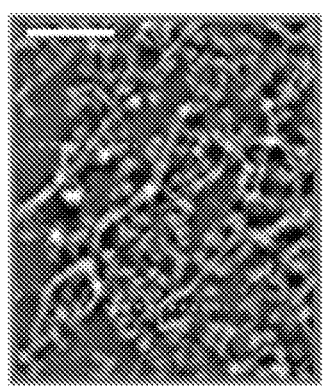
Figure 43B:
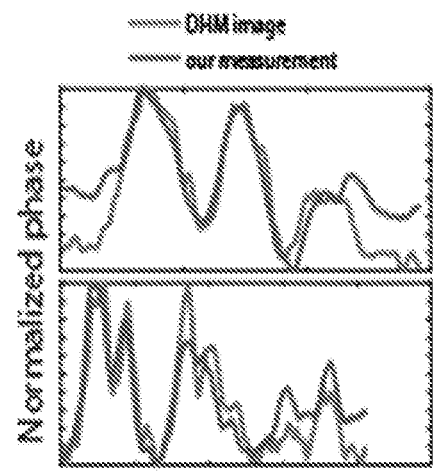
Figure 43C:
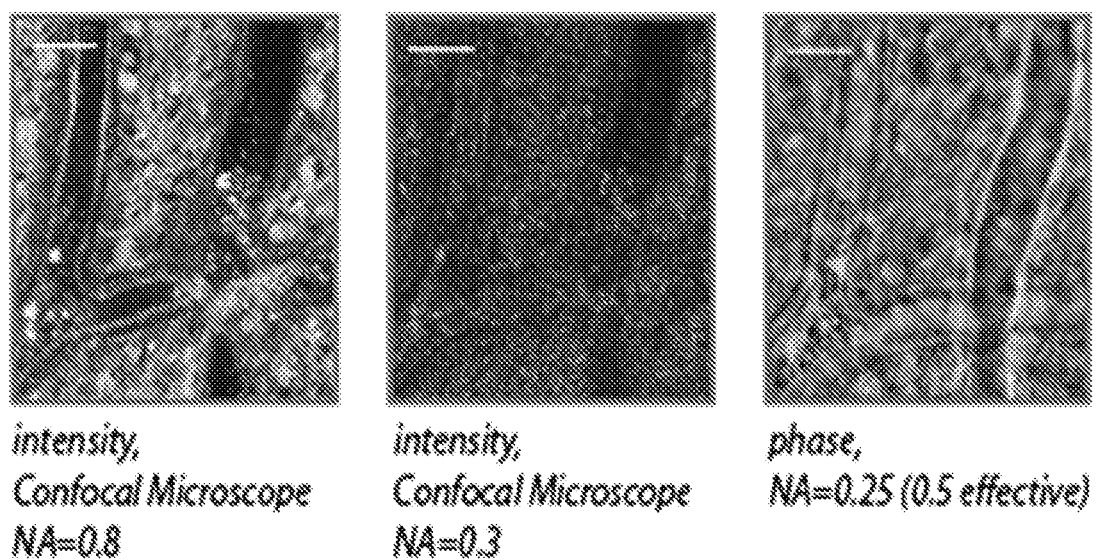
Figure 44:
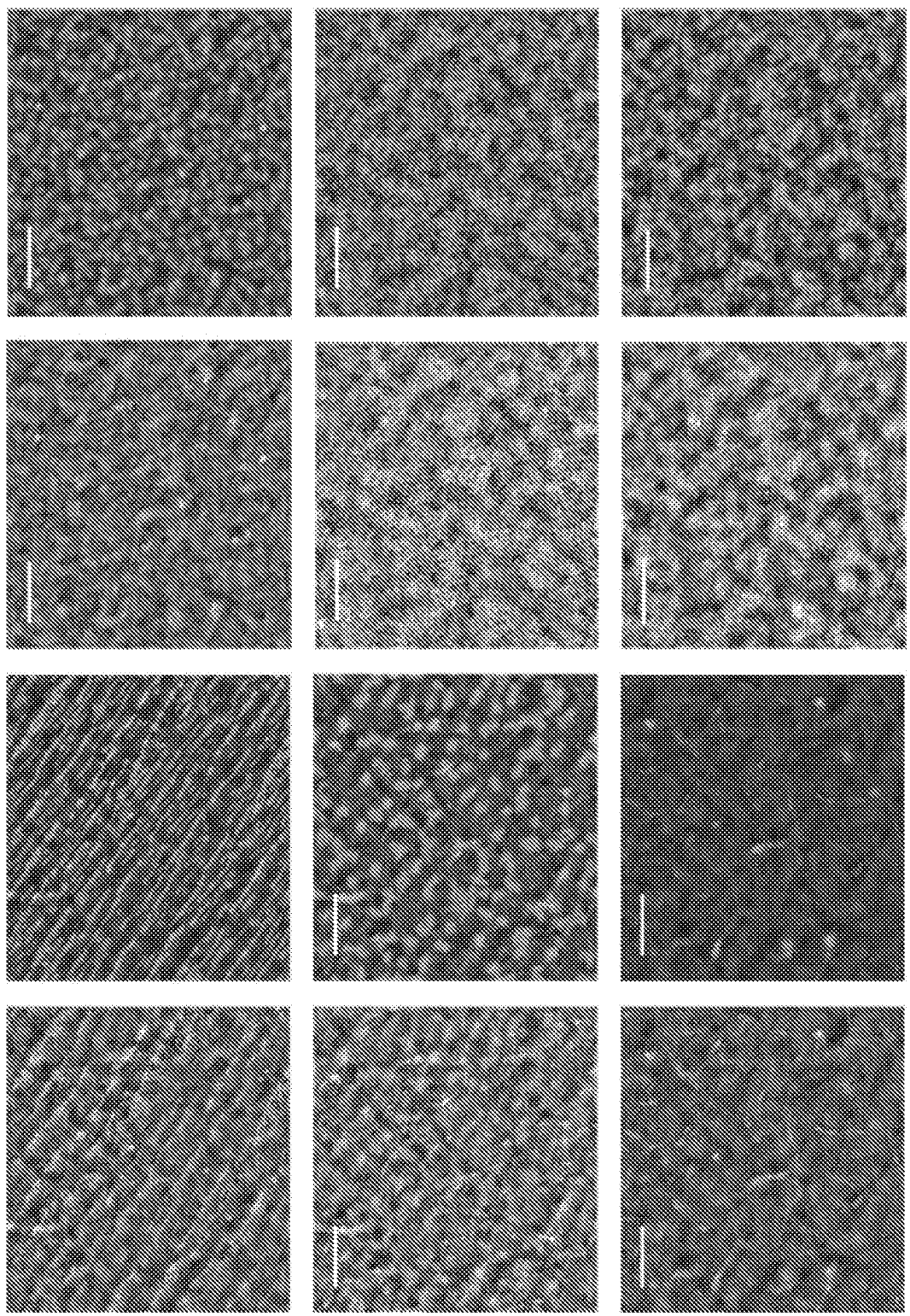
FIG. 44 depicts different phase measurement scanning a thick pig retina sample (180 um) in depth. The pictures show the different layers of the retina.
Figure 45:
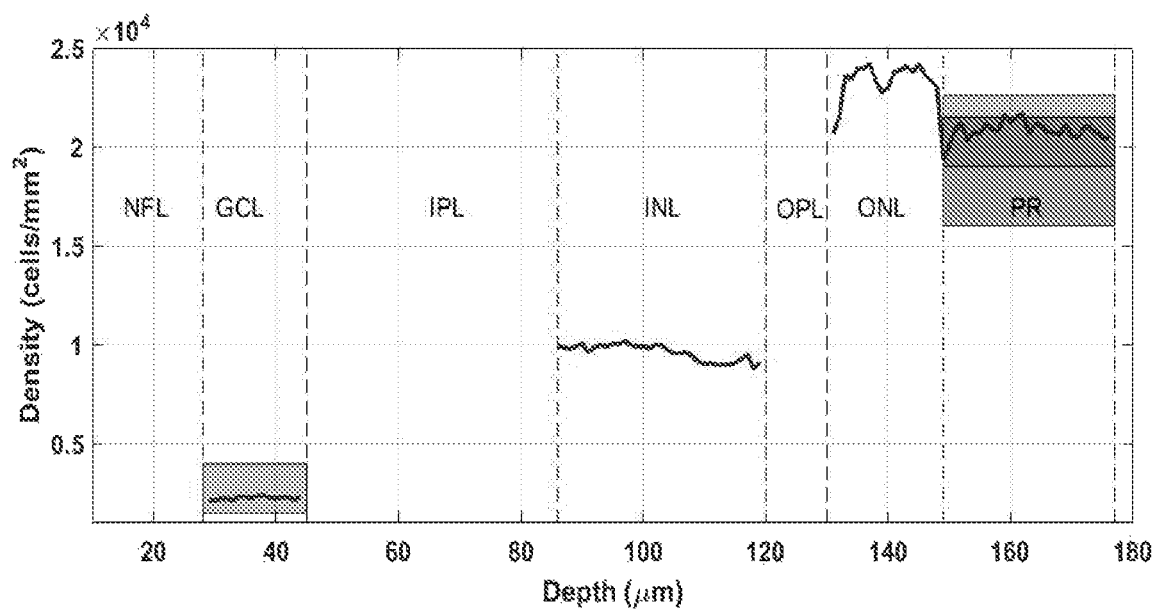
FIG. 45 shows a graph that represents a computation of cells density for different layer based on the scan of FIG. 44.

With respect to measurements related to ex vivo phase imaging, referring to FIG. 42, a microscope has been built having similar parameters to the in-vivo imaging case. It includes an oblique illumination being scattered first by a scattering plate, a reflecting layer the provide the backscattered light, a microscope objective, an imaging lens and a camera. FIG. 43 shows the ex-vivo measurement results, with the resolution assessment, a comparison of the image obtained with the invention and a digital holographic microscope providing a quantitative phase image. FIG. 43 also shows a comparison with images acquired with a confocal microscope providing intensity images. FIGS. 44 and 45 show the results of a scan in depth of a pig retina, with the different layer of the retina, and computing the cells density for the layers of nucleus.

Figure 32:
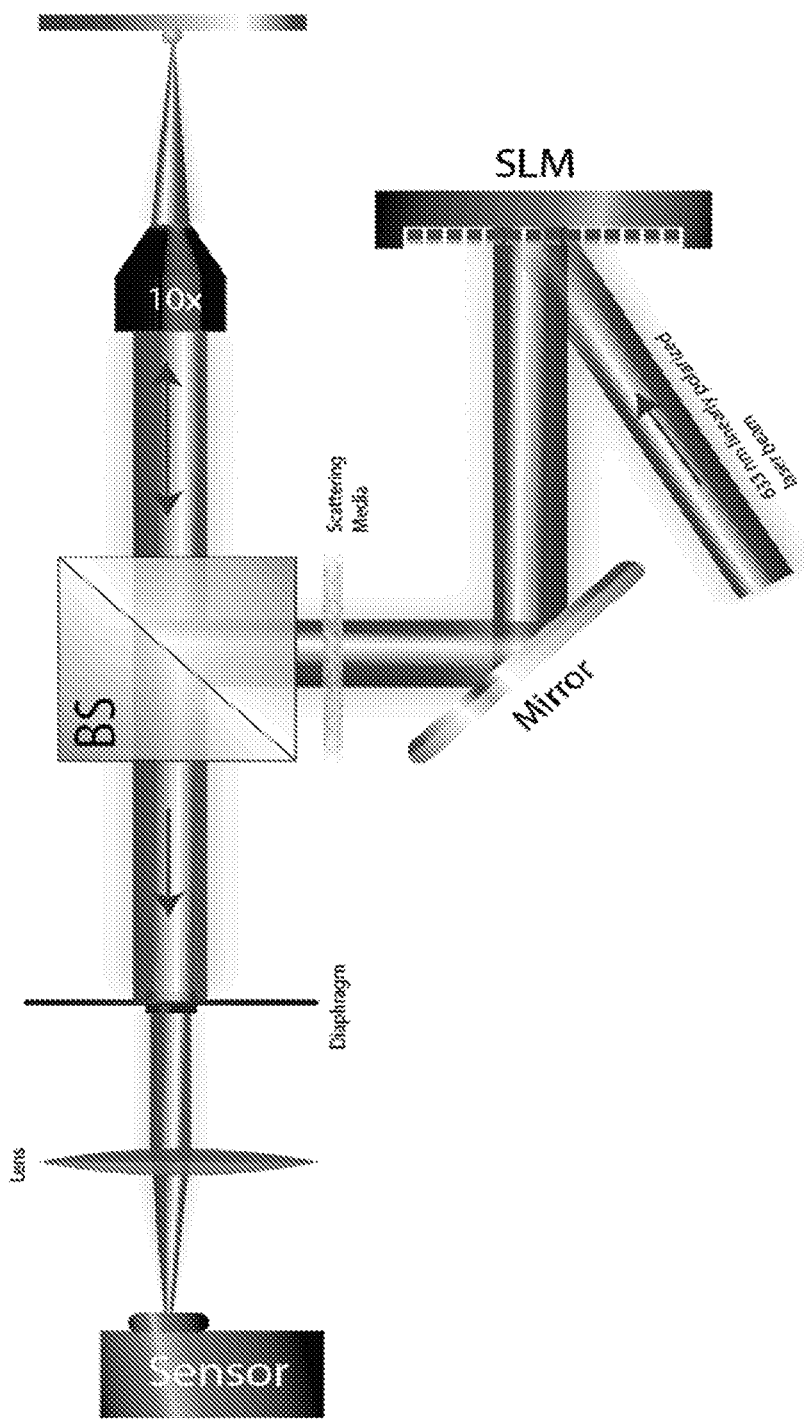
FIG. 32 shows a representation of the optical scheme used for focusing scattered light on a bead, according to an aspect of the present invention.
Figure 33A:
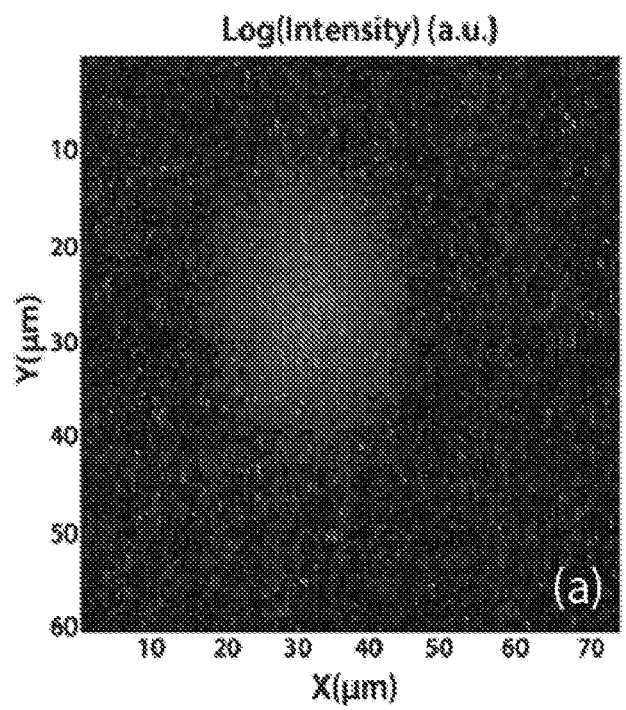
FIG. 33A-33D shows intensity enhancement of a single bead using the presented method, according to an aspect.
Figure 33B:
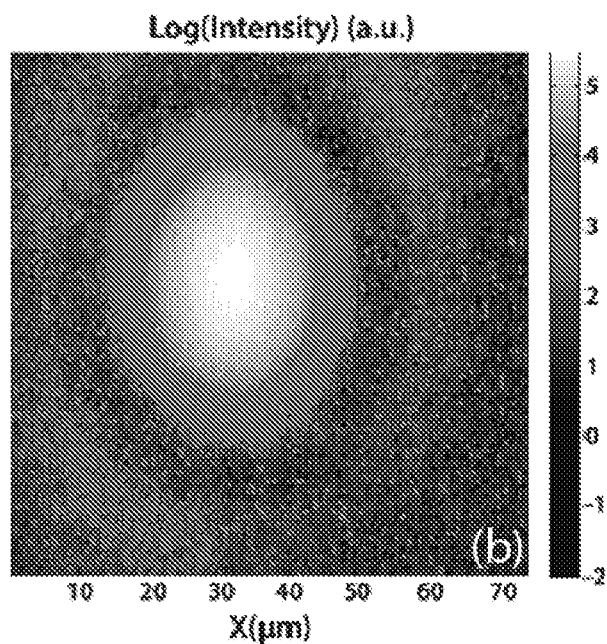
Figure 33C:
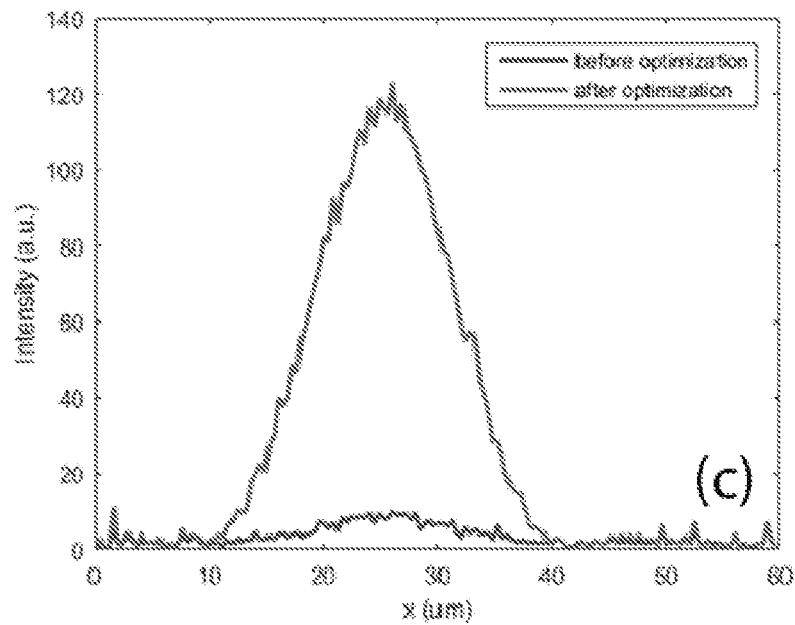
Figure 33D:
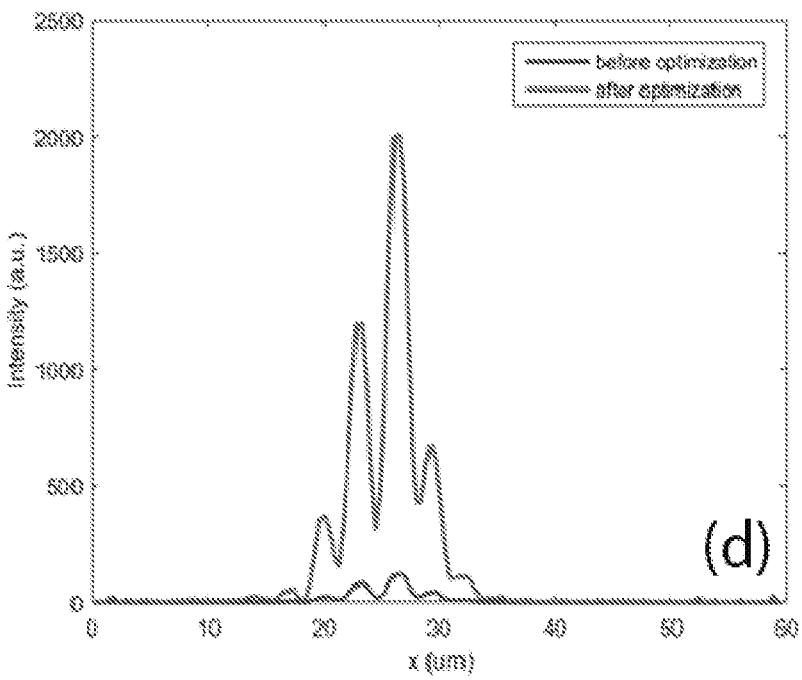

Next, measurement have been performed for the operability and proof of principle demonstration using wavefront shaping. For proof of principle demonstration, we use a static sample of microbeads and a liquid crystal based spatial light modulator to optimize the feedback light. This system is shown in FIG. 32. The linearly polarized collimated laser beam illuminates the SLM before passing through a 400 μm thick scattering layer. Next, the scattered beam illuminates the sample through a 0.25 NA objective. The reflected light is collected by the objective, and passes through a diaphragm in order to artificially decrease the NA of the detection to mimic the limited resolution of the eye pupil. The sample of microbeads is used to reproduce the situation of high reflectivity features that the detection system cannot resolve.

FIG. 33 shows the results of the focusing process performed for one 10 μm diameter bead, and a detection NA of 0.02. The procedure is as follow: An image was recorded with the maximum resolution (curve before optimization in FIG. 33D), then the diaphragm is closed to optimize the wavefront (FIG. 33C). The low resolution PSF before and after optimization is shown in FIG. 33C. Finally, we open the diaphragm to record the optimized high resolution PSF (curve after optimization in FIG. 33D). Two-dimensional images before (FIG. 33A) and after optimization (FIG. 33B) are shown. For a sample of several beads, the focusing is not as good as the one bead case, so we develop a method to discriminate the beads thanks to the shape of their PSF. If two beads are closer than the resolution distance the collected image would be similar to the PSF. Anyway, the ratio between the maximum and the total energy will change depending on the distance between the centers. This parameter can be used to discriminate between the one bead and the multiple beads cases.

Various applications can be performed with the present device, system, and method. Applications include quantitative phase imaging of the retinal layer on top of the photoreceptors, between the inner and external limiting membranes, for example inner limiting membrane (ILM), retinal nerve fiber layer (RNFL), ganglion cell layer (GCL), inner plexiform layer (IPL), inner nuclear layer (INL), outer plexiform layer (OPL), outer nuclear layer (ONL), external limiting membrane (ELM).

Next, the proposed method can provide dark field images of the choroid and RPE (retinal pigmented epithelium), allowing for imaging of the choroidal tumors with enhanced contrast and choroidal microvasculature.

Finally, recording two dark field images allows obtaining phase gradient information of the retinal layers.

In sum, with the aspects of the present invention, a vision process for the eye is determined by the very first layers of retina. Before reaching the photoreceptor cells, light entering the eye needs to pass through a layer having a thickness of approximately 100 µm of ganglion and neurons cells forming the retina. These cells are phase object and so difficult to see with standard imaging techniques. Indeed, phase imaging methods usually need the illumination system to be on the opposite side of the sample with respect to the imaging system, making this impossible to perform in-vivo. However, the possibility of performing phase imaging from one side using properties of scattering media has been shown.

According to aspects of the present invention, a system is proposed for performing qualitative as well as quantitative imaging in the fundus of the eye with oblique illumination. The use of different illumination points, through the pupil, on the sclera itself or directly on the skin covering the sclera, provides, due to through the scattering properties of the eye, oblique back-illumination, allowing for phase contrast images. These phase contrast images can be used to reconstruct pictures containing only phase or absorption information. Furthermore, the same illumination scheme can be used for collecting dark field images from the pupil. Moreover, the use of incoherent illumination allows doubling the resolution of the recovered image compared to coherent imaging.

In the present application, it has been shown that phase contrast can be obtained and how the absolute absorption and phase profile can be obtained for two dimensions (2D) and three dimensions (3D). With several embodiments, different illumination modes have been shown to provide phase-contrast and different apparatus for providing this illumination and acquiring a picture. Algorithms have been discussed for reconstructing 2D and 3D phase and absorption profiles. In addition, secondary information has been discussed that can be obtained with this technique and different improvements.

While the invention has been disclosed with reference to certain preferred embodiments, numerous modifications, alterations and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

REFERENCES

U.S. Pat. No. 7,387,385
U.S. Pat. Pub. No. 2007/0159600
U.S. Pat. Pub. No. 2007/0030448
U.S. Pat. No. 3,954,392
U.S. Pat. No. 4,200,362
Medibell Medical Vision Technologies Ltd.—Panoret 1000-Wide-Angle Digital Retinal Camera, printed at least as early as October 2002.
A. Schalenbourg, L. Zografos "Pitfalls in colour photography of choroidal tumours." Eye. 2013; 27(2):224-229
Devrim Toslak, Damber Thapa, Yanjun Chen, Muhammet Kazim Erol, R. V. Paul Chan, and Xincheng Yao, "Transpalpebral illumination: an approach for wide-angle fundus photography without the need for pupil dilation," Opt. Lett. Vol. 41, pp. 2688-2691 (2016)
D. Scoles, Y. N. Sulai and A. Dubra "In vivo dark-field imaging of the retinal pigmentepithelium cell mosaic," Biomed. Opt. Exp. Vol. 4, 9, pp. 1710-1723 (2013)
T. Y. P. Chui, D. A. VanNasdale, and S. A. Burns, "The use of forward scatter to improve retinal vascular imaging with an adaptive opticsscanning laser ophthalmoscope," Biomed. Opt. Exp. Vol. 3, 10, pp. 2537-2549 (2012)
T. Y. P. Chui, T. J. Gast, and S. A. Burns, "Imaging of Vascular Wall Fine Structure in the Human Retina Using Adaptive Optics Scanning Laser Ophthalmoscopy," Invest Ophthalmol VisSci. vol. 54, pp. 7115-7124 (2013)
T. N Ford, K. K Chu and J. Mertz, "Phase-gradient microscopy in thick tissue with oblique back-illumination," Nat. Methods, Vol. 9, 12 (2012)
S. B. Mehta and C. J. R. Sheppard, "Quantitative phase-gradient imaging at high resolution with asymmetric illumination-based differential phase contrast," Opt. Lett. 34, 13, pp. 1924-1926 (2009)
L. Tian and L. Waller, "Quantitative differential phase contrast imaging in an LED array microscope," Opt. Exp. 23, 9, pp. 11394-11403 (2015)
Z. Liu, S. Liuand, L. Waller "Real-time brightfield, darkfield, and phase contrast imaging in a light emitting diode array microscope," Journal of Biomed. Opt. 19, 10, 106002 (2014)
Int. Pat. Pub. No. WO 2013/148360
Int. Pat. Pub. No. WO 2015/179452
G. Zheng, R. Horstmeyer, and C. Yang, "Wide-field, high-resolution Fourier ptychographic microscopy," Nature photonics, Vol. 7, Iss. 9, 2013, pp. 739-745.
U.S. Pat. No. 8,731,272
U.S. Pat. Pub. No. 2004/0189941
European Pat. No. EP 1427328
U.S. Pat. No. 7,364,296
M. Vellekoop and A. P. Mosk, "Focusing coherent light through opaque strongly scattering media," Opt. Lett. 32, 2309-2311 (2007)
H. Yilmaz, E. G. van Putten, J. Bertolotti, A. Lagendijk, W. L. Vos, and A. P. Mosk, "Speckle correlation resolution enhancement of wide-field fluorescence imaging," Optica 2, 424-429 (2015)
U.S. Pat. No. 8,717,574

The invention claimed is:

1. A method for imaging a tissue of an eye, the method comprising the steps of:
providing an oblique illumination chosen among a transscleral illumination and a transepidermal illumination to the eye by at least one of a plurality of light emitting areas of a light delivery device, the plurality of light emitting areas being independently controllable and arranged to direct light towards the tissue of the eye;

causing an output beam from light scattered from a fundus of the eye by the oblique illumination;

capturing the output beam with an imaging system to acquire a sequence of images of the fundus of the eye, said sequence of image being processed to obtain pictures of said tissue of the eye, said sequence of images of the fundus of the step of capturing is obtained by sequentially turning on one or more of the plurality of light emitting areas at a time in the step of providing the oblique illumination, and wherein the method further comprises a step of measuring at least one of aberrations of the eye and correcting the aberrations with an aberration correction method in order to increase the resolution of said sequence of images acquired after oblique illumination.

2. The method of claim 1, wherein the tissue of the eye is part of a living eye of a human or an animal, the light delivery device is configured for at least one of the following illumination modalities:

no contact between the light delivering device and a face of a patient of the eye;

the light delivering device is in contact with a skin surrounding the eye;

the light delivering device is in contact with a sclera of the eye; and the light delivering device is in contact with a cornea of the eye.

3. The method of claim 1, wherein the tissue of the eye includes an ex vivo sample from the eye of a human or an animal.

4. The method of claim 1, wherein the oblique illumination is formed by at least one of a diverging beam, a collimated beam, a focused beam, and a structured illumination.

5. The method of claim 1, wherein the tissue of the eye includes to at least one of an in vivo retina of a human, an ex vivo retina of a human, an in vivo retina of a human, and an in vivo retina of an animal, and wherein the step of capturing includes at least one modality of a darkfield illumination, a darkfield collection, a focused coherent illumination by wavefront shaping, and an oblique optical coherence tomography by a low coherence source.

6. The method of claim 1, wherein in the step of capturing, the sequence of images is captured with at least one of a 2D single frame acquisition and a 2D lock-in acquisition.

7. The method of claim 1, wherein the tissue of the eye is an anterior eye tissue, and wherein in the step of providing the oblique illumination, the illumination is obtained by backreflection from at least one of the fundus of the eye and the iris of the eye.

8. A system for imaging a tissue of an eye, the system comprising:

a light delivering device having a plurality of light emitting areas, at least one of the light emitting areas being directed towards the tissue of the eye for providing oblique illumination chosen among a transscleral illumination and a transepidermal illumination, an output beam caused by light scattered off a fundus of the eye of the oblique illumination from said light emitting areas;

an imaging system configured to capture the output beam and to acquire a sequence of images of the fundus of the eye; and a controller configured to individually control the light emitting areas of light delivering device, to sequentially turn on one of the plurality of light emitting areas at a time, for capturing the sequence of images by the imaging system, wherein the system further comprises means for measuring at least one of aberrations of the eye and means for correcting the measured aberrations in order to increase the resolution of said sequence of images acquired after oblique illumination.

9. The system of claim 8, wherein light from the light delivering device has a transmission range of a sclera-choroid-skin in a wavelength range between 400 nm and 1200 nm, and wherein the light delivering device uses light coming from one or more of the different types of light sources.

10. The system of claim 8, wherein the imaging system includes a scanning system and a detector, the scanning system having a collection pupil that is either centered or shifted with respect to a center of a pupil of the eye, and the detector includes at least one of a single pixel detector, a line camera, a two-dimensional multipixel device and a split detector.

11. The system of claim 8, wherein the sequence of images is acquired by imaging the tissue of the eye on a two-dimensional multipixel device.

12. The system of claim 8, wherein the light delivering device comprises plurality of waveguides.

13. The system of claim 8, wherein at least one part of the system is in contact with a face of a patient, preferably said part being chosen among a head holder, a chin holder and a light delivering device, said part being covered with a removable disposable part.

14. The system of claim 8, further comprising:

an optical system including a different ophthalmic imaging system to provide multimodal imaging of the eye tissues.

15. The method of claim 1, wherein in the step of capturing, the sequence of images is captured with a scanning acquisition system.

16. The method of claim 1, wherein said pictures are chosen among dark field image, phase contrast image or absorption contrast image.

17. The method of claim 1, wherein the image acquisition is adapted depending on the picture of the fundus to be obtained, for instance one light emitting area to obtain dark field picture, or at least two light emitting areas for phase contrast picture.

18. The method of claim 1, wherein the images acquired are processed to reconstruct picture containing phase and/or absorption information for instance by a phase and absorption retrieval algorithm.

* * * * *